(12) United States Patent
Huang et al.

(10) Patent No.: US 9,955,943 B2
(45) Date of Patent: ***May 1, 2018

(54) WINDOWED TIME-REVERSAL MUSIC TECHNIQUE FOR SUPER-RESOLUTION ULTRASOUND IMAGING

(71) Applicant: LOS ALAMOS NATIONAL SECURITY, LLC, Los Alamos, NM (US)

(72) Inventors: Lianjie Huang, Los Alamos, NM (US); Yassin Labyed, Los Alamos, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 874 days.

This patent is subject to a terminal disclaimer.

(21) Appl. No.: 14/339,780

(22) Filed: Jul. 24, 2014

(65) Prior Publication Data

US 2014/0364738 A1 Dec. 11, 2014

Related U.S. Application Data

(63) Continuation of application No. PCT/US2013/024512, filed on Feb. 1, 2013.

(Continued)

(51) Int. Cl.
*A61B 8/00* (2006.01)
*A61B 8/08* (2006.01)
(Continued)

(52) U.S. Cl.
CPC .............. *A61B 8/0825* (2013.01); *A61B 8/13* (2013.01); *A61B 8/5207* (2013.01);
(Continued)

(58) Field of Classification Search
None
See application file for complete search history.

(56) References Cited

U.S. PATENT DOCUMENTS 4,075,883 A 2/1978 Glover
4,582,065 A 4/1986 Adams
(Continued)

FOREIGN PATENT DOCUMENTS

JP 2009189867 A 8/2009
KR 1020100075011 A 7/2010
(Continued)

OTHER PUBLICATIONS

Devaney et al. Super-resolution Processing of Multi-static Data Using Time Reversal and Music. 2000. [Online]: http://www.ece.neu.edu/faculty/devaney/ajd/preprints.htm. (pp. 4, 10).*

(Continued)

*Primary Examiner* — Jonathan Cwern
(74) *Attorney, Agent, or Firm* — Lewis Roca Rothgerber Christie LLP

(57) ABSTRACT

Systems and methods for super-resolution ultrasound imaging using a windowed and generalized TR-MUSIC algorithm that divides the imaging region into overlapping sub-regions and applies the TR-MUSIC algorithm to the windowed backscattered ultrasound signals corresponding to each sub-region. The algorithm is also structured to account for the ultrasound attenuation in the medium and the finite-size effects of ultrasound transducer elements.

13 Claims, 35 Drawing Sheets

Related U.S. Application Data

(60) Provisional application No. 61/594,966, filed on Feb. 3, 2012.

(51) Int. Cl.
    *A61B 8/13*     (2006.01)
    *G01S 7/52*     (2006.01)
    *G01S 15/89*     (2006.01)

(52) U.S. Cl.
    CPC ...... *G01S 7/52046* (2013.01); *G01S 15/8977* (2013.01); *A61B 8/5253* (2013.01); *G01S 7/52095* (2013.01); *G01S 15/8915* (2013.01); *G01S 15/8997* (2013.01)

(56) References Cited

U.S. PATENT DOCUMENTS

| | | | |
|---|---|---|---|
| 5,465,722 A * | 11/1995 | Fort | G01H 5/00 600/437 |
| 6,186,951 B1 | 2/2001 | Lizzi | |
| 2001/0020130 A1 | 9/2001 | Gee | |
| 2002/0099290 A1 | 7/2002 | Haddad | |
| 2002/0173722 A1 | 11/2002 | Hoctor | |
| 2003/0158481 A1 | 8/2003 | Stotzka | |
| 2004/0034307 A1 | 2/2004 | Johnson et al. | |
| 2006/0058678 A1 | 3/2006 | Vitek | |
| 2006/0173304 A1 | 8/2006 | Wang | |
| 2006/0184020 A1 | 8/2006 | Sumi | |
| 2006/0293597 A1 | 12/2006 | Johnson et al. | |
| 2007/0100239 A1 | 5/2007 | Nair | |
| 2008/0045864 A1 | 2/2008 | Candy | |
| 2008/0081993 A1 | 4/2008 | Waki | |
| 2008/0229832 A1 | 9/2008 | Huang | |
| 2008/0294043 A1 | 11/2008 | Johnson et al. | |
| 2008/0319318 A1 | 12/2008 | Johnson et al. | |
| 2009/0076389 A1 | 3/2009 | Jin | |
| 2009/0099456 A1 | 4/2009 | Burcher | |
| 2010/0157732 A1 | 6/2010 | Saenger et al. | |
| 2011/0118984 A1 | 5/2011 | Chevion | |
| 2011/0125014 A1 | 5/2011 | Derode | |
| 2011/0131020 A1 | 6/2011 | Meng | |

FOREIGN PATENT DOCUMENTS

| | | |
|---|---|---|
| WO | WO2007133882 A2 | 11/2007 |
| WO | WO2011103303 A2 | 8/2011 |

OTHER PUBLICATIONS

Szabo et al. 2004. Determining the pulse-echo electromechanical characteristic of a transducer using flat plates and point targets. The Journal of the Acoustical Society of America, vol. 116 No. 1, p. 91.*

Cobbold. (2007). Foundations of Biomedical Ultrasound. New York: Oxford University Press. (pp. 110-111).*

Yao et al. A Fast Algorithm to Calculate Ultrasound Pressure Fields From Single-Element Transducers. 1989. IEEE Transactions on Ultrasonics, Ferroelectrics and Frequency Control, vol. 36 No. 4, p. 446.*

Lemoult et al. Time Reversal in Subwavelength-Scaled Resonant Media: Beating the Diffraction Limit. 2011. International Journal of Microwave Science and Technology, vol. 2011, Article ID 425710, p. 4.*

Waag et al. A Ring Transducer System for Medical Ultrasound Research. 2006. IEEE Transactions on Ultrasonics, Ferroelectrics, and Frequency control. vol. 53 No. 10, p. 1709.*

Labyed et al. Ultrasound Time-Reversal Music Imaging With Diffraction and Attenuation Compensation. 2012. IEEE Transactions on Ultrasonics, Ferroelectrics, and Frequency Control, vol. 59 No. 10, p. 2188.*

Nguyen et al. The DORT solution in acoustic inverse scattering problem of a small elastic scatterer. 2010. Ultrasonics, vol. 50 Issue 8, pp. 831, 832.*

Devaney et al. Time-reversal-based imaging and inverse scattering of multiply scattering point targets. 2005. The Journal of the Acoustical Society of America, vol. 118 No. 5, p. 3132.*

Korean Intellectual Property Office (KIPO), International Search Report and Written Opinion dated May 30, 2013, Counterpart PCT International Application No. PCT/US2013/024512, pp. 1-10, with claims searched, pp. 11-21.

Korean Intellectual Property Office (KIPO), International Search Report and Written Opinion dated May 30, 2013, PCT International Application No. PCT/US2013/024550, pp. 1-11, with claims searched, pp. 12-21.

Office action dated May 2, 2017 issued in co-pending U.S. Appl. No. 14/339,728.

Office action dated Mar. 31, 2017 issued in co-pending U.S. Appl. No. 14/339,712.

Office action dated Apr. 4, 2017 issued in co-pending U.S. Appl. No. 14/339,738.

Office action dated May 10, 2017 issued in co-pending U.S. Appl. No. 14/339,791.

Office action dated May 1, 2017 issued in co-pending U.S. Appl. No. 14/339,759.

Office action dated Apr. 19, 2017 issued in co-pending U.S. Appl. No. 14/339,770.

Anagaw et al., "Full Waveform Inversion with Total Variation Regularization," Recovery—2011 CSPG CSEG CWLS Convention, pp. 1-4.

Boonyasiriwat et al., 3D Multisource Full-Waveform Inversion using Dynamic Random Phase Encoding,: Society of Exploration Geophysics Technical Program Expanded Abstracts, 2010, pp. 1044-1049.

Cuiping, Li et al., "In Vivo Breast Sound-Speed Imaging with Ultrasound Tomography," Ultrasound in Medicine and Biology, Oct. 2009, vol. 35, No. 10, pp. 1616-1628.

Duric et al. "Development of Ultrasound Tomography for Breast Imaging: Technical Assessment," Medical Physics 32(5):1375-86.

Fichtner et al. "Full Seismic Waveform Tomography for upper-mantle structure in the Australasian region using Adjoint Methods," Geophys, J. Int. (2009) 179, pp. 1703-1725.

Huang et al., "A Rapid and Robust Numerical Algorithm for Sensitivity Encoding with Sparsity Constraints: Self-Feeding Sparse SENSE," Magnetic Resonance in Medicine, 2010, 64:1078-1088.

Ikedo et al., Development of a fully automatic scheme for detection of masses in whole breast ultrasound images, 2007, Medical Physics, vol. 24, No. 11, pp. 4381.

Margrave et al., Full Waveform Inversion with Wave Equation Migration and Well Control, CREWES Research Report vol. 22, 2010, pp. 1-20.

Sallard et al.. "Use of a priori Information for the Deconvolution of Ultrasonic Signals," Rev. of Prog. in Quantitative Nondestructive Evaluation, vol. 17, Plenum Press, New York, 1998, pp. 735-742.

Sumi, C., "Spatially variant regularization for the Deconvolution of Ultrasonic Signals," Rev. of Prog. in Quantitative Nondestructive Evaluation, J Med Ultrasonics (2007) 34:125-131, Mar. 8, 2007.

Tai, et al. "Image Denoising Using TV-Stokes Equation with an Orientation-Matching Minimization" Space and Variational Methods in Computer Vision, Lecture Notes in Computer Science, vol. 5567, 2009, pp. 1-12.

Tape et al., "Finite-Frequency Tomography Using Adjoint Methods-Methodology and Examples Using Membrane Surface Waves," Geophys. J. Int. (2007) 168, pp. 1105-1129.

Korean Intellectual Property Office (KIPO) International Search Report and Written Opinion dated Jun. 2, 2013, PCT International Application No. PCT/US2013/024676, pp. 1-10, with claims searched, pp. 11-18.

Korean Intellectual Property Office (KIPO) International Search Report and Written Opinion dated May 30, 2013, PCT International Application No. PCT/US2013/024545, pp. 1-12, with claims searched, pp. 13-20.

(56) References Cited

OTHER PUBLICATIONS

Korean Intellectual Property Office (KIPO) International Search Report and Written Opinion dated May 30, 2013, Counterpart PCT International Application No. PCT/US2013/024656, pp. 1-10, with claims searched, pp. 11-16.
Korean Intellectual Property Office (KIPO) International Search Report and Written Opinion dated May 30, 2013, PCT International Application No. PCT/US2013/024662, pp. 1-10, with claims searched, pp. 11-19.
Korean Intellectual Property Office (KIPO) International Search Report and Written Opinion dated May 30, 2013, PCT International Application No. PCT/US2013/024539, pp. 1-16, with claims searched, pp. 17-24.

* cited by examiner

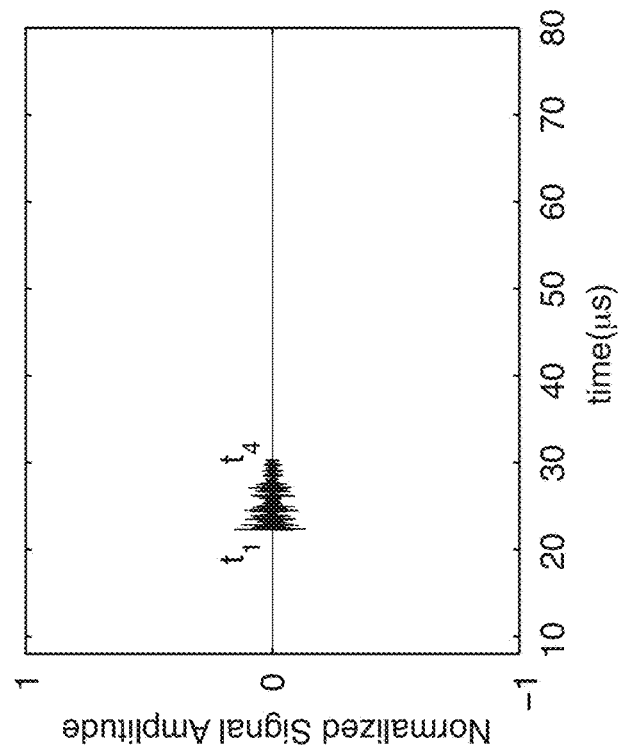
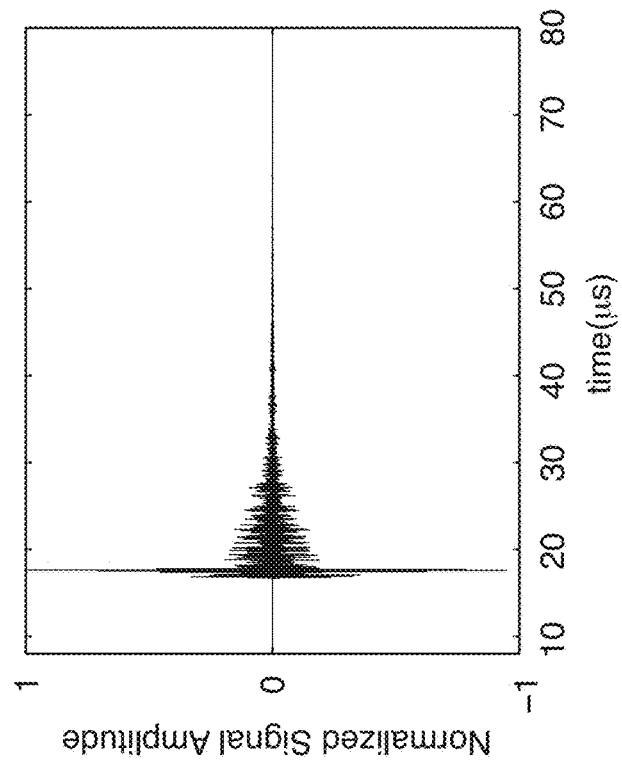

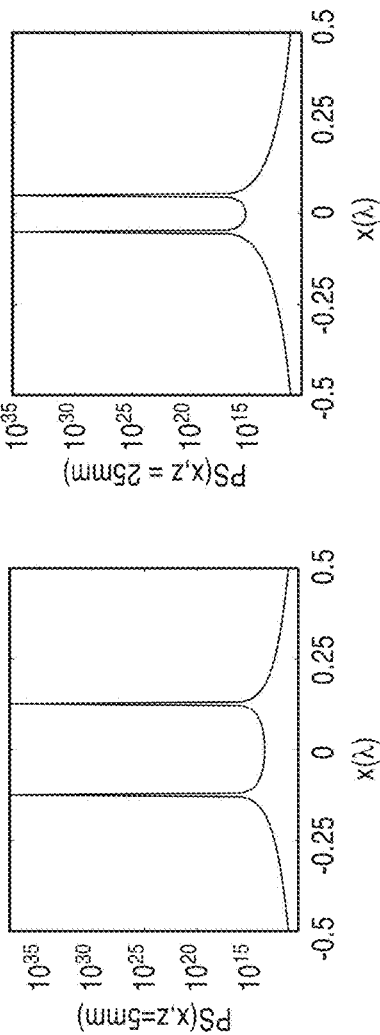
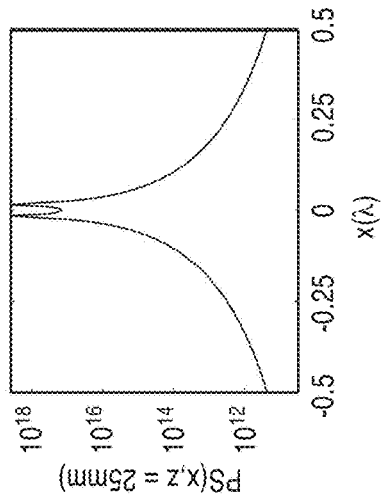
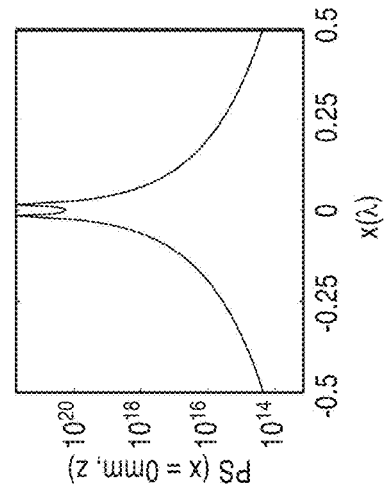
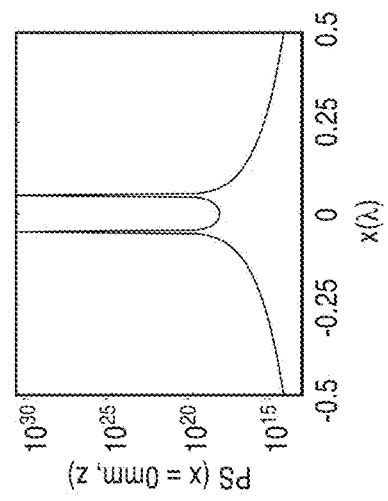
FIG. 11A  FIG. 11B  FIG. 11C
FIG. 11D  FIG. 11E  FIG. 11F

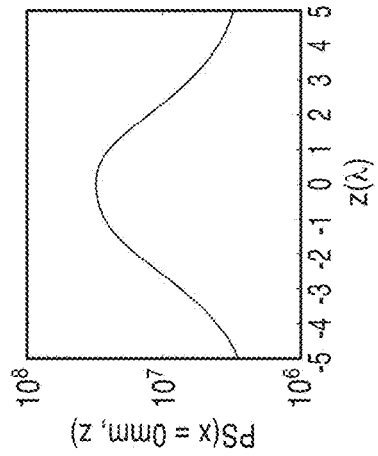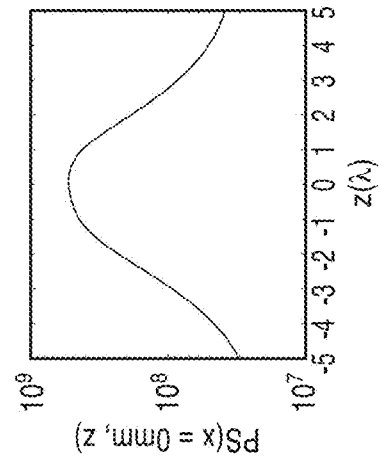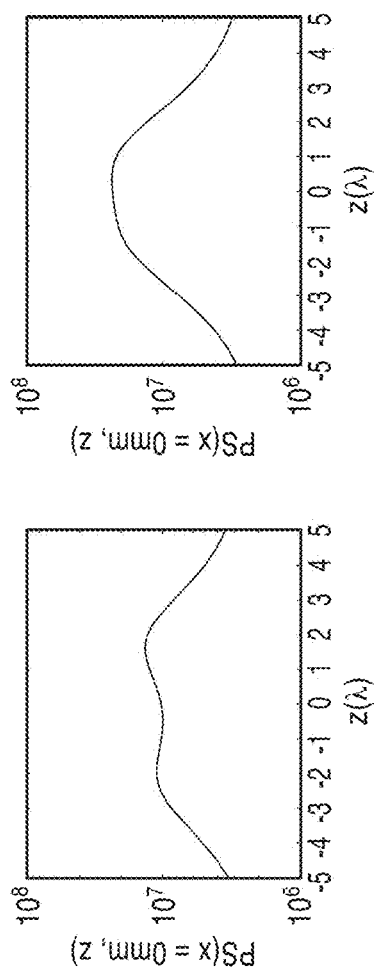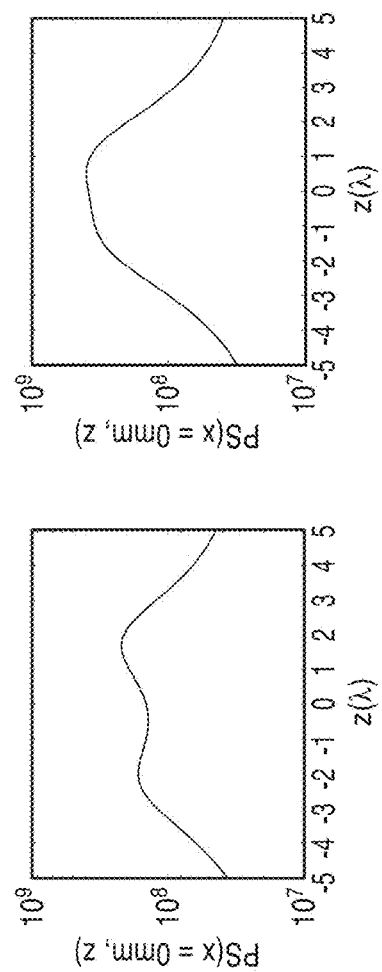

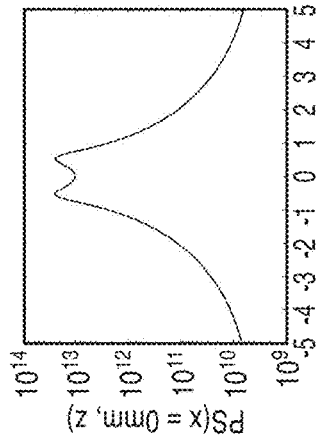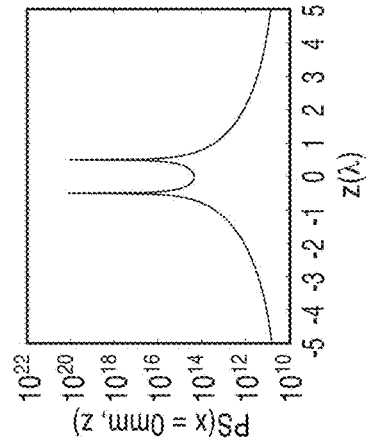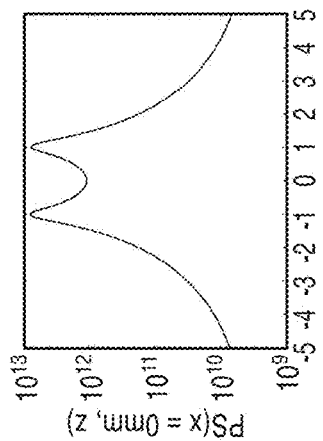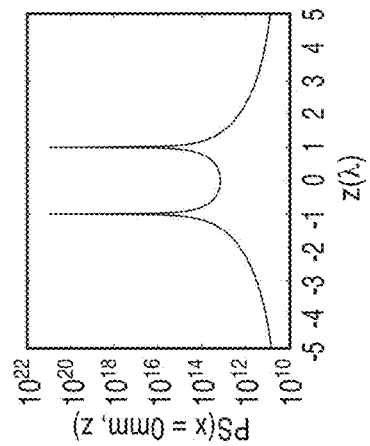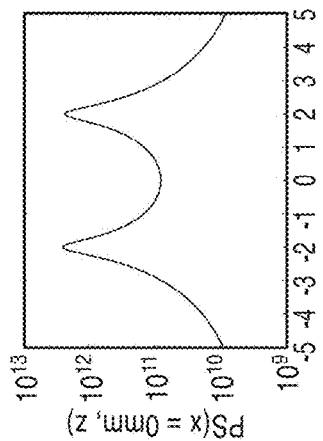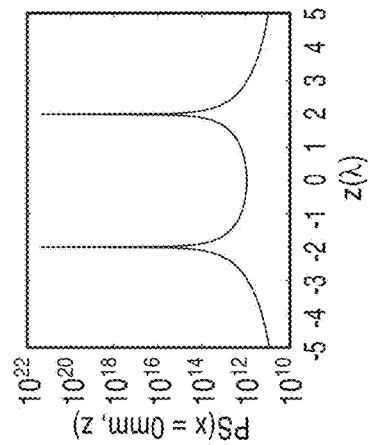

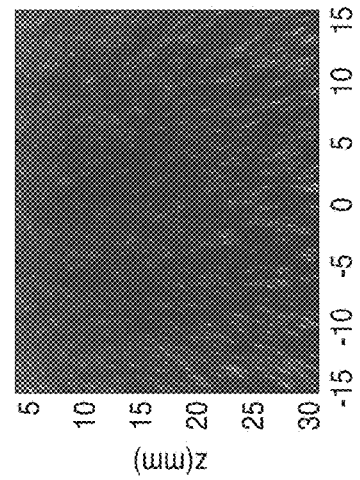
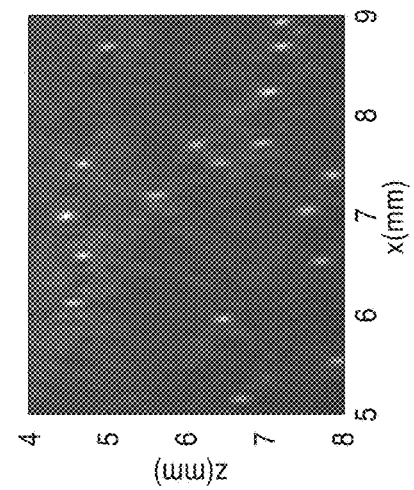
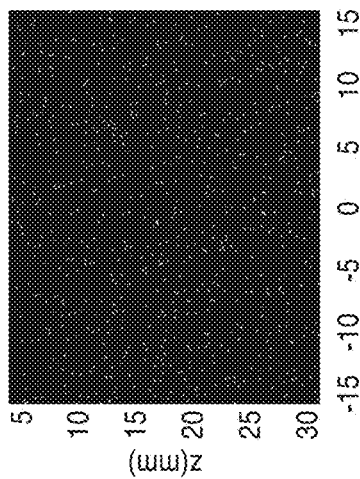
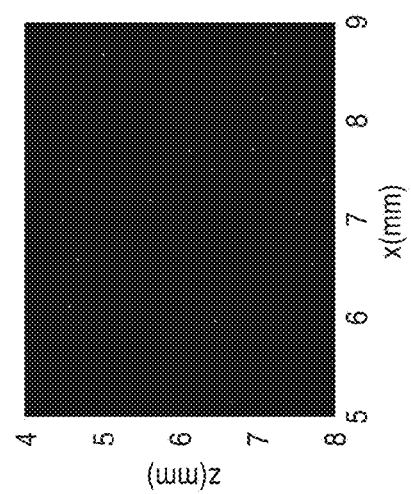
FIG. 18A
FIG. 18B
FIG. 18C
FIG. 18D

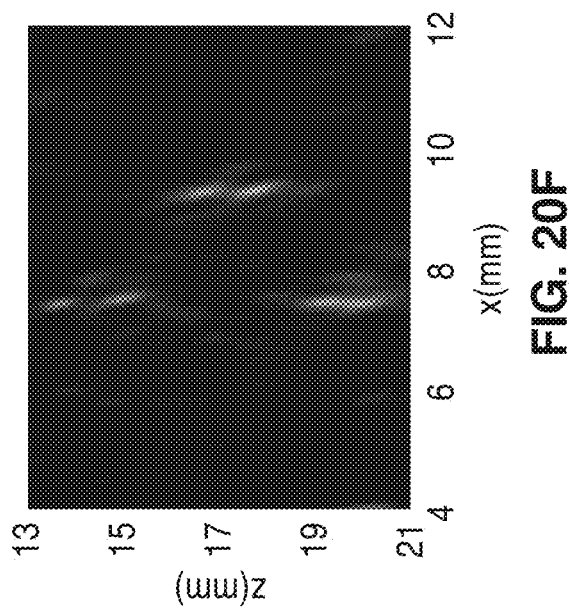
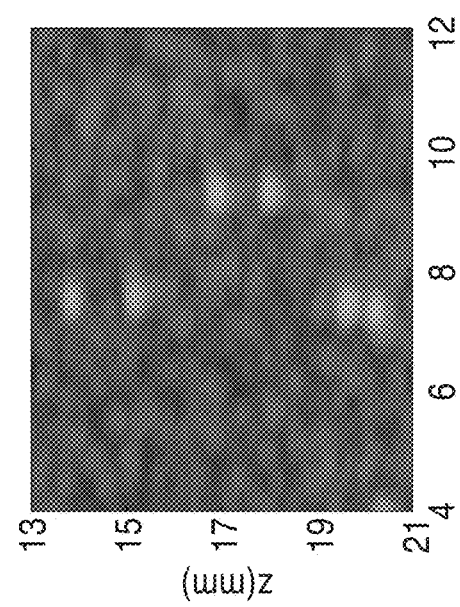

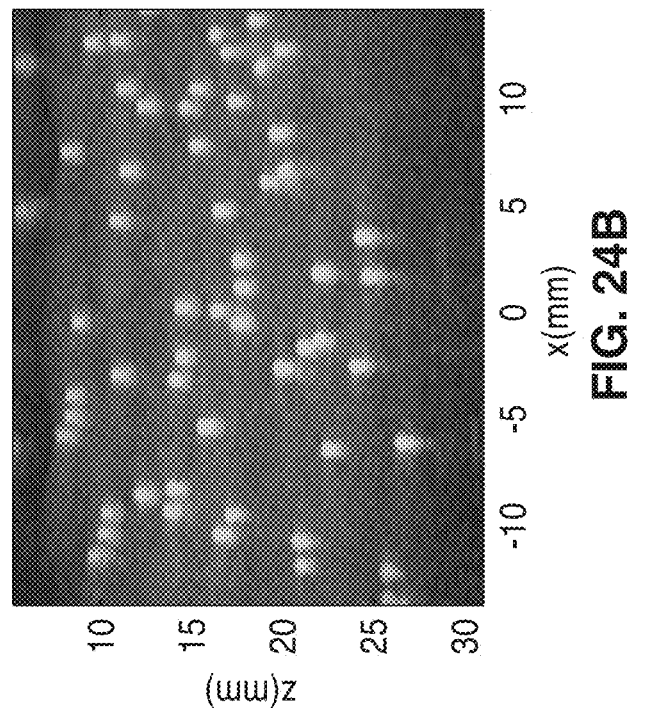
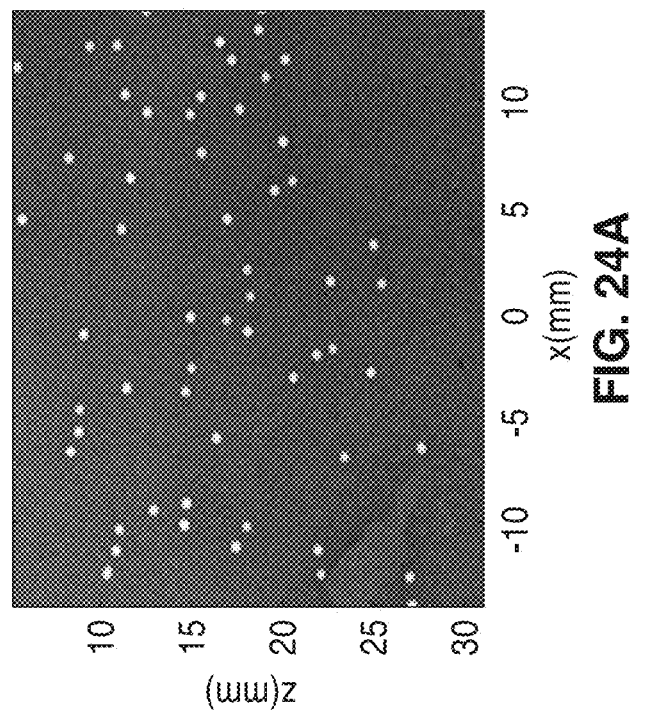

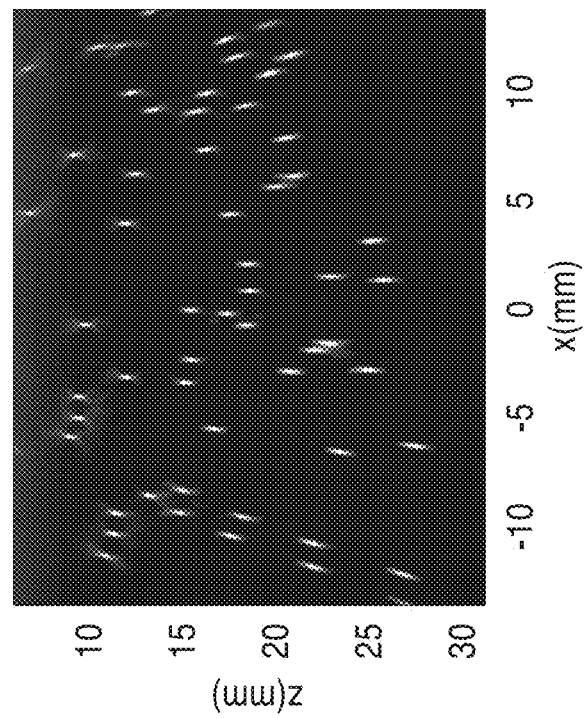
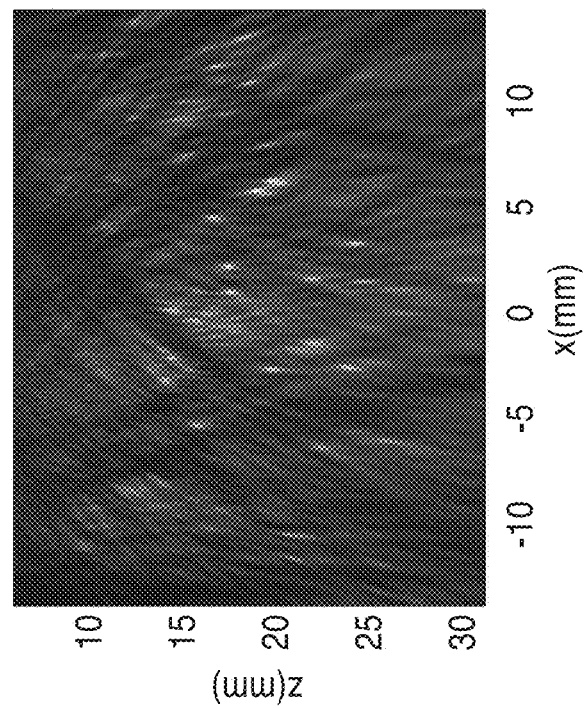

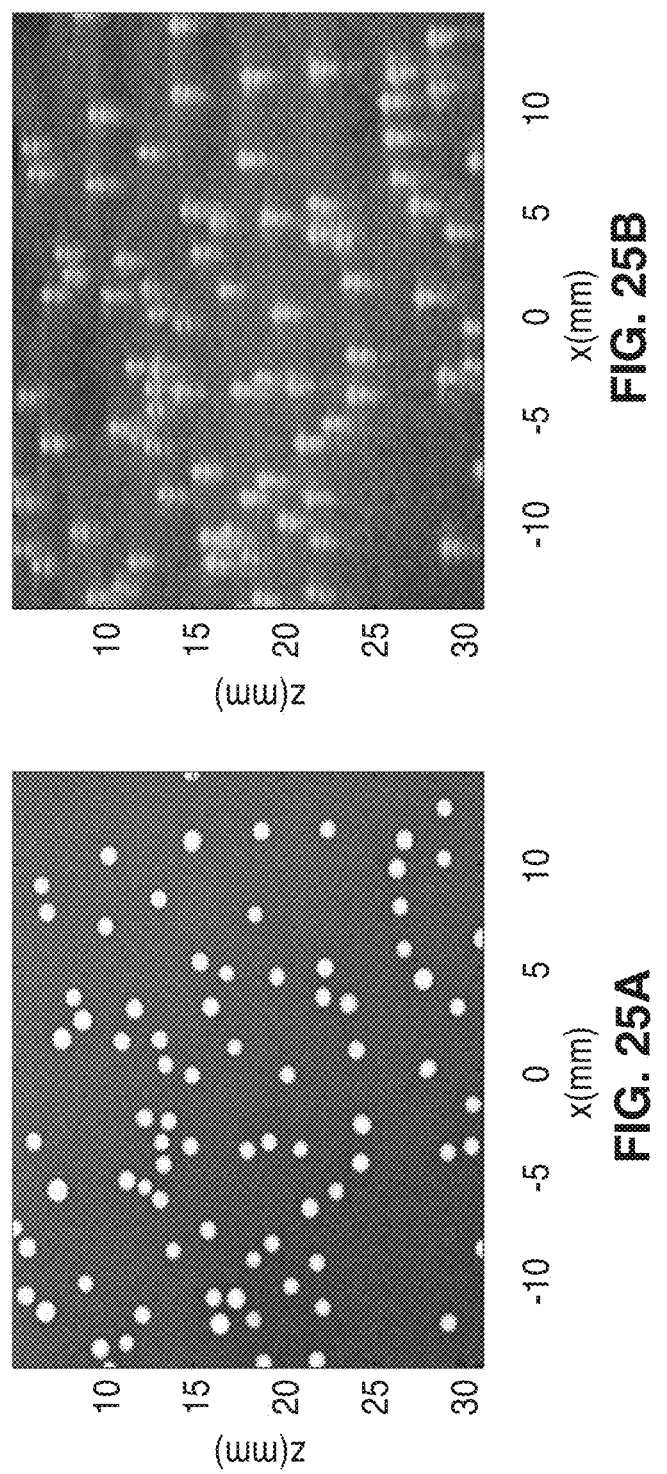

WINDOWED TIME-REVERSAL MUSIC TECHNIQUE FOR SUPER-RESOLUTION ULTRASOUND IMAGING

CROSS-REFERENCE TO RELATED APPLICATIONS

This application is a 35 U.S.C. § 111(a) continuation of PCT international application number PCT/US2013/024512 filed on Feb. 1, 2013, incorporated herein by reference in its entirety, which claims priority to, and the benefit of, U.S. provisional patent application Ser. No. 61/594,966 filed on Feb. 3, 2012, incorporated herein by reference in its entirety. Priority is claimed to each of the foregoing applications.

The above-referenced PCT international application was published as PCT International Publication No. WO 2013/116783 on Aug. 8, 2013, incorporated herein by reference in its entirety.

STATEMENT REGARDING FEDERALLY SPONSORED RESEARCH OR DEVELOPMENT

This invention was made with Government support under Contract No. DE-AC52-06NA25396 awarded by the Department of Energy. The Government has certain rights in the invention.

INCORPORATION-BY-REFERENCE OF COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to imaging and more particularly to ultrasound imaging.

2. Description of Related Art

Time-reversal (TR) methods have received considerable interest in many areas, with applications ranging from the destruction of kidney stones, to the detection of flaws in solids, and to ultrasound medical imaging. One of these methods is the Time-Reversal with Multiple Signal Classification (TR-MUSIC) imaging algorithm developed by Devaney. This algorithm combines TR focusing with the MUSIC signal-subspace algorithm.

Numerical and experimental studies that used the MUSIC algorithm with TR imaging showed that when the targets are much smaller than the ultrasound wavelength, images with sub-wavelength resolution can be achieved. The high-resolution capability of TR-MUSIC imaging may find many applications in medical ultrasound. One area of interest is the detection of breast micro-calcifications, which are the first sign of breast cancer for more than half of all breast cancer cases.

The TR-MUSIC algorithm assumes that the ultrasound attenuation of the medium is negligible, and does not account for the finite-size effects of the transducer elements. In addition, the algorithm is applicable only when the number of point scatterers is fewer than the number of elements in a transducer array.

Accordingly, an object of the present invention is a generalized TR-Music method to account for ultrasound tissue attenuation and the finite-size effects of transducer elements. Another object is a windowed TR-MUSIC method for imaging point scatterers when their number exceeds the number of ultrasound transducers in the scanner array, or imaging extended targets. At least some of these objectives will be met in the description below.

BRIEF SUMMARY OF THE INVENTION

Time-reversal imaging with Multiple Signal Classification (TR-MUSIC) is an algorithm for detecting small targets embedded in a medium. This algorithm can produce images with sub-wavelength resolution when the targets are point-like, and when the number of scatterers is fewer than the number of ultrasound transducer elements used to interrogate the medium.

The system and methods of the present invention are directed to a new algorithm based on TR-MUSIC for imaging point scatterers when their number exceeds the number of ultrasound transducer elements used to interrogate the medium, or when the medium contains numerous extended targets that cannot be considered as point scatterers.

In a preferred embodiment, the methods of the present invention divide the imaging region into overlapping sub-regions and apply the TR-MUSIC algorithm to the windowed backscattered ultrasound signals corresponding to each sub-region. The images of all sub-regions are then combined to form the total image by interpolation of the images from the overlapped sub-regions.

Imaging results comprised of numerical and phantom data show that when the number of scatterers within each sub-region is much smaller than the number of ultrasound transducer elements, the methods of the present invention yield super-resolution images with accurate scatterer localization.

The generalized TR-MUSIC algorithm of the present invention is also structured to account for the ultrasound attenuation in the medium and the finite-size effects of the ultrasound transducer elements. The generalized TR-MUSIC algorithm yields higher-resolution ultrasound images compared to those obtained without accounting for the ultrasound attenuation or the finite-size effects of ultrasound transducer elements.

The axial and lateral resolutions of the algorithm of the present invention were evaluated with respect to the effect of noise on the resolution of the images. Computer simulations and tissue-mimicking phantom data were acquired with a real-time synthetic-aperture ultrasound system to demonstrate the improved capability of the windowed TR-MUSIC algorithm. The windowed time-reversal MUSIC technique has the potential to detect breast microcalcifications.

In accordance with a preferred method of the present invention, the TR-MUSIC algorithm is generalized to account for the ultrasound attenuation in the interrogated medium, and the finite-size effects of the transducer elements.

In a preferred embodiment, a windowed TR-MUSIC algorithm is also used to image point scatterers with high resolution, even when their number exceeds the number of transducer elements.

Compared with the original MUSIC method, the generalized TR-MUSIC method of the present invention includes the following new features:

1) Accounts for the ultrasound attenuation in the tissue. This is accomplished by introducing the complex wavenumber in Eq. 4. The complex wavenumber contains the amplitude attenuation coefficient.

2) Accounts for the finite-size effects of ultrasound transducer elements. This is achieved by the integration in Eq. 16. In contrast, the original MUSIC method uses a point source Green's function.

3) Accounts for the electro-mechanical responses (time response) and their variations in the element-to-element sensitivity, as described in the calibration method 84 shown in FIG. 5.

The generalized TR-MUSIC technique of the present invention takes the above three aspects into account.

In one embodiment of the present invention, the windowing method is incorporated into the generalized TR-MUSIC method. The original TR-MUSIC technique is valid only when the number of small (point) scatterers is fewer than the number of ultrasound transducer elements. The windowed TR-MUSIC method of the present invention can produce super-resolution images even when the number of small (point) scatterers exceeds the number of ultrasound transducer elements, and when the imaging plane contains numerous extended targets.

The windowed TR-MUSIC method of the present invention uses ultrasound data acquired using a synthetic-aperture ultrasound system. The investigational synthetic-aperture ultrasound system of the present invention allows acquisition of patient ultrasound data in real time. In the system, each element of the transducer array transmits ultrasound sequentially, and all elements in the transducer array simultaneously record ultrasound signals scattered from the tissue after each element is fired. The features of the system and method of the present invention provide a real-time synthetic-aperture system that can be used for patient data acquisition.

In a synthetic-aperture ultrasound system, ultrasound from each element of a transducer array or a virtual source of multiple elements propagates to the entire imaging domain, and all elements in the transducer array receive ultrasound signals reflected/scattered from the imaging region. Therefore, synthetic-aperture ultrasound data contain information of ultrasound reflected/scattered from all possible directions from the imaging domain to the transducer array. In contrast, the conventional ultrasound system records only 180° backscattered signals.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

FIG. 8E is a plot of a received time signal.

FIG. 8F is a plot of the resulting time signal after muting the time samples outside the time window that starts at time $t_1$ and ends at time $t_4$.

Figure 10A:
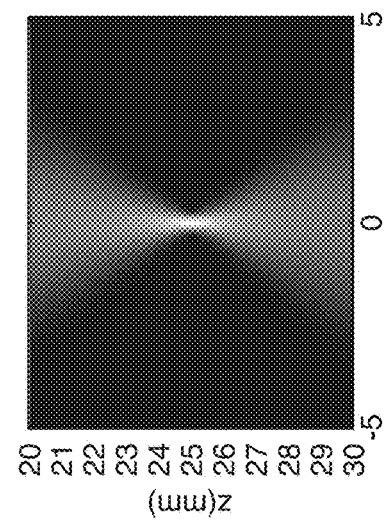
Figure 10B:
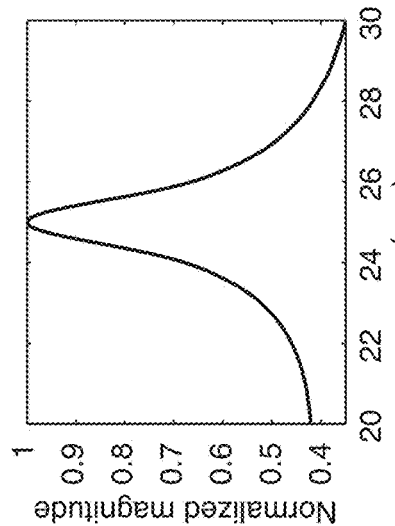
Figure 10C:
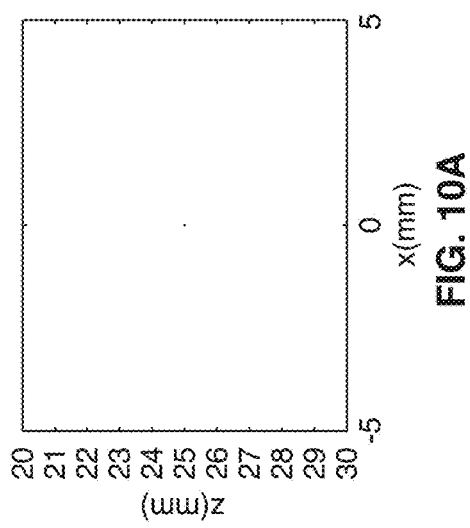
Figure 10D:
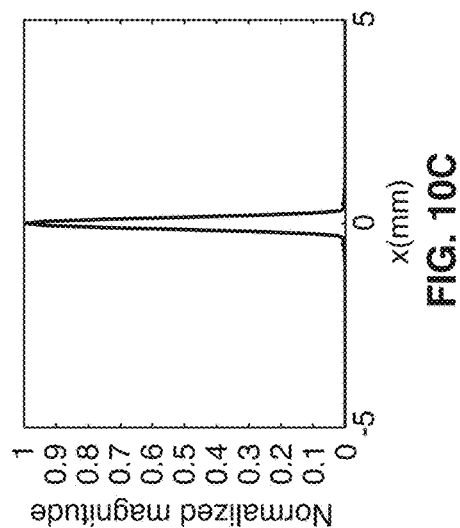

FIG. 10A through FIG. 10D show simulation geometry for a point source (black dot shown in FIG. A) and the transducer array elements. FIG. 10B is the CPSF for the point source in the plot of FIG. 10A. FIG. 10C shows the Lateral profile of the CPSF at z=25 mm. FIG. 10D shows the axial profile of the CPSF at x=0 mm.

FIG. 11A through FIG. 11C are plots showing axial profiles at z=25 mm for the pseudo-spectra of two point scatterers separated axially by $\lambda/4$, $\lambda/10$, and $\lambda/30$, respectively, where $\lambda$ is the ultrasound wavelength.

FIG. 11D through FIG. 11F are plots showing lateral profiles at x=0 mm for the pseudo-spectra of two point scatterers separated laterally by $\lambda/4$, $\lambda/10$, and $\lambda/30$, respectively, where $\lambda$ is the ultrasound wavelength.

Figure 12A:
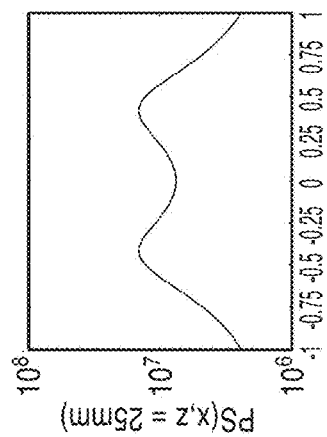
Figure 12B:
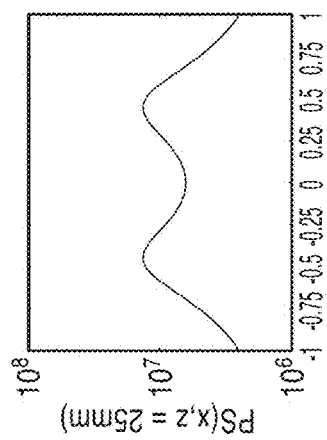
Figure 12C:
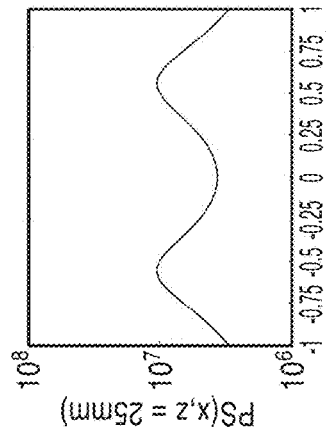

FIG. 12A through FIG. 12C show lateral profiles at z=25 mm for the noise-free pseudo-spectra of two point scatterers separated laterally by (a) $\lambda$, (b) $\lambda/2$, (c) and $\lambda/4$, where $\lambda$ is the ultrasound wavelength.

Figure 12D:
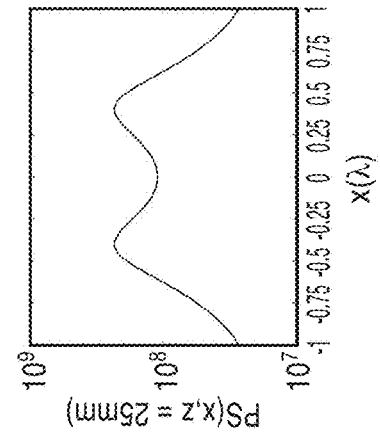
Figure 12E:
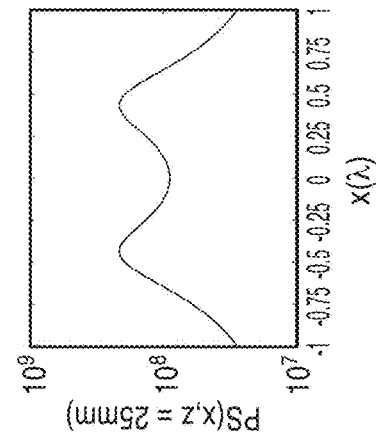
Figure 12F:
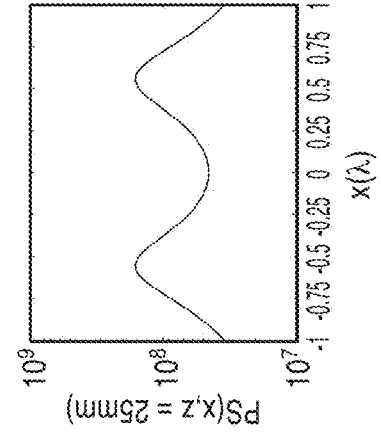

FIG. 12D through FIG. 12F show plots of the profiles corresponding to FIG. 12A to FIG. 12C when attenuation is compensated.

Figure 12G:
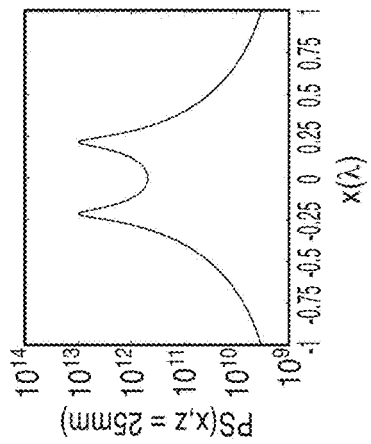
Figure 12H:
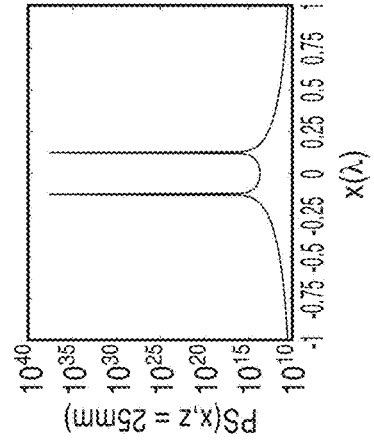
Figure 12I:
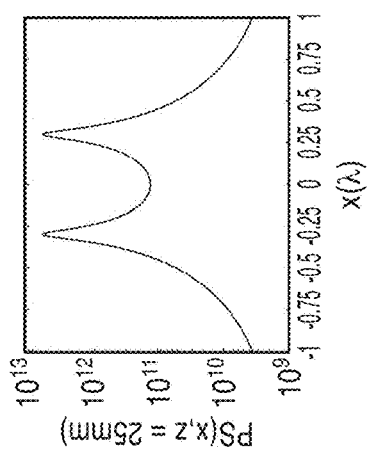

FIG. 12G through FIG. 12I show plots of the profiles corresponding to FIG. 12A FIG. 12C when diffraction effects are compensated.

Figure 12J:
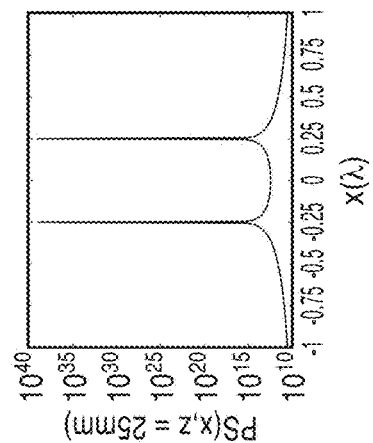
Figure 12K:
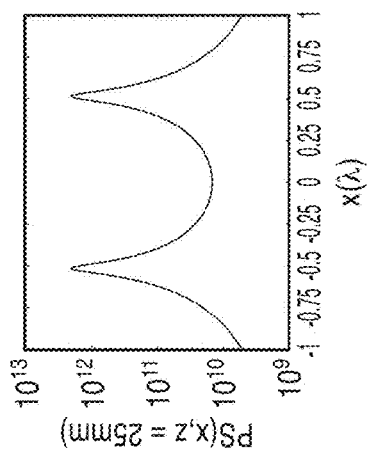
Figure 12L:
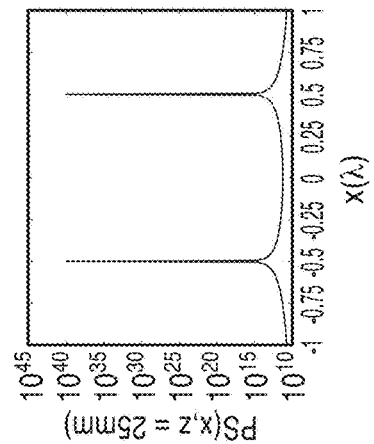

FIG. 12J through FIG. 12L show plots of the profiles corresponding to FIG. 12A through FIG. 12C when both attenuation and diffraction effects are compensated FIG. 13A through FIG. 13C show axial profiles at x=0 mm for the pseudo-spectra of two point scatterers separated axially by (a) 4$k$, (b) 2$k$, (c) and X, where $\lambda$ is the ultrasound wavelength.

FIG. 13D through FIG. 13F show plots of the profiles corresponding to FIG. 13A through FIG. 13C when attenuation is compensated.

FIG. 13G through FIG. 13I show plots of the profiles corresponding to FIG. 13A through FIG. 13C when diffraction effects are compensated.

FIG. 13J through FIG. 13L show plots of the profiles corresponding to FIG. 13A through FIG. 13C when both attenuation and diffraction effects are compensated.

Figure 14A:
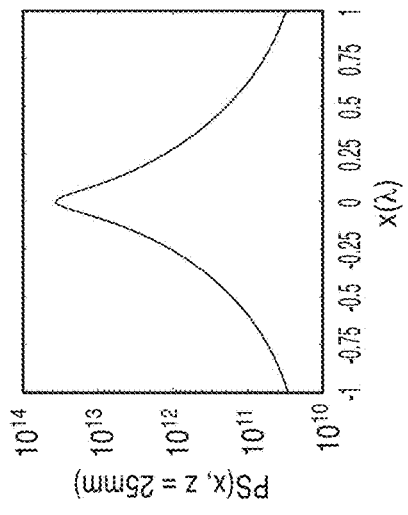
Figure 14B:
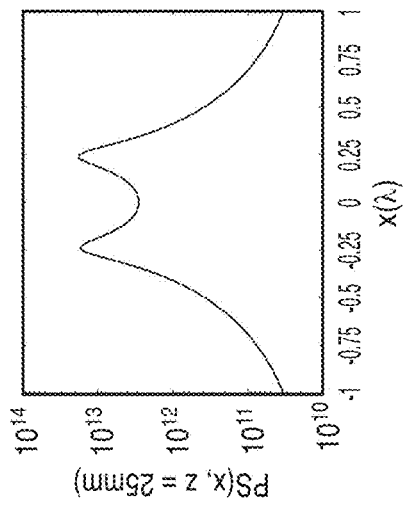
Figure 14C:
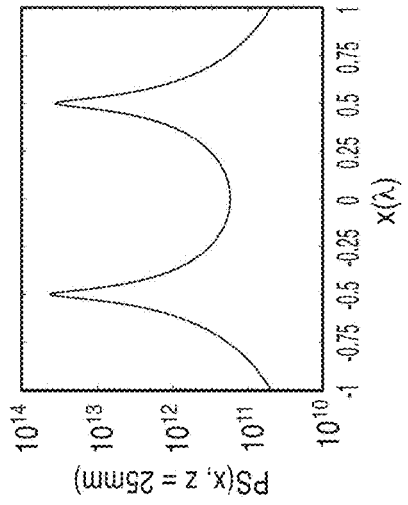
Figure 14D:
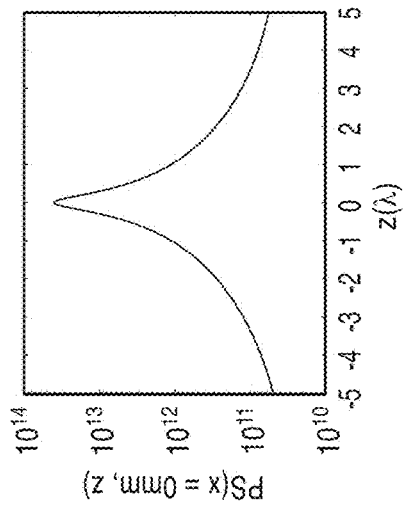
Figure 14E:
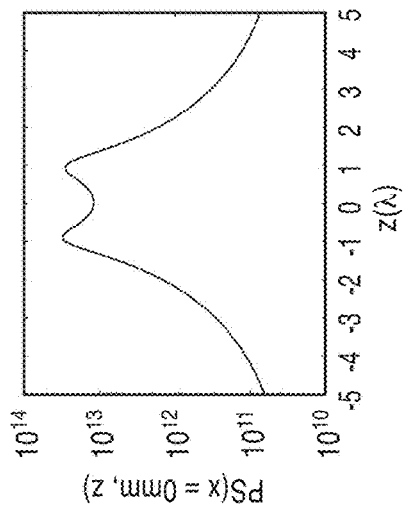
Figure 14F:
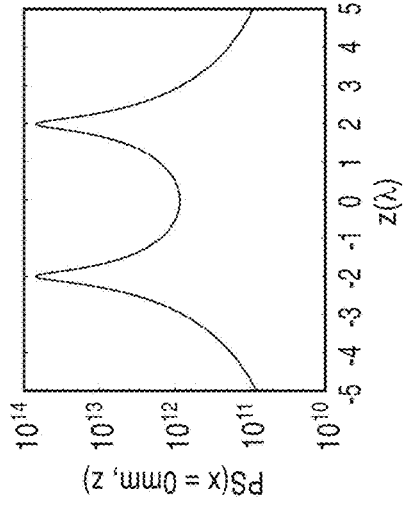

FIG. 14A through FIG. 14F show profiles when zero-mean Gaussian noise added to the recorded signals (SNR=25 dB). The plots of FIG. 14A through FIG. 14C show lateral profiles at x=0 mm for the pseudo-spectra of two point scatterers separated laterally by $\lambda$, $\lambda/2$, and $\lambda/4$, respectively, where $\lambda$ is the ultrasound wavelength. The plots of FIG. 14D through FIG. 14F show axial profiles at z=25 mm for the pseudo-spectra of two point scatterers separated axially by $4\lambda$, $2\lambda$, and $\lambda$, respectively.

Figure 15A:
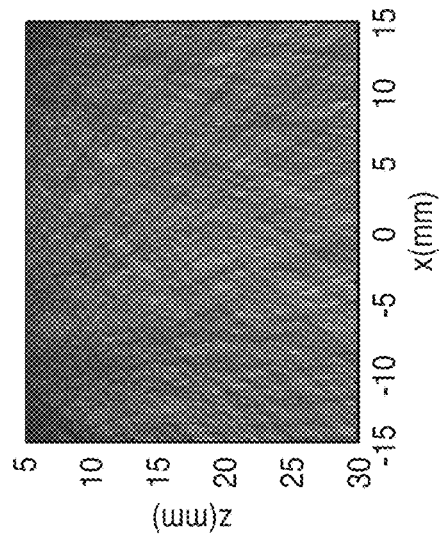

FIG. 15A is an image showing simulation geometry for 1000 randomly distributed scatterers.

Figure 15B:
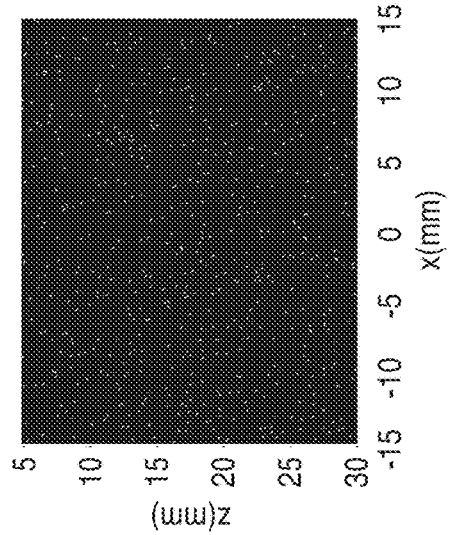

FIG. 15B is an image of the pseudo-spectrum calculated using the 20 eigenvectors with the lowest eigenvalues.

Figure 15C:
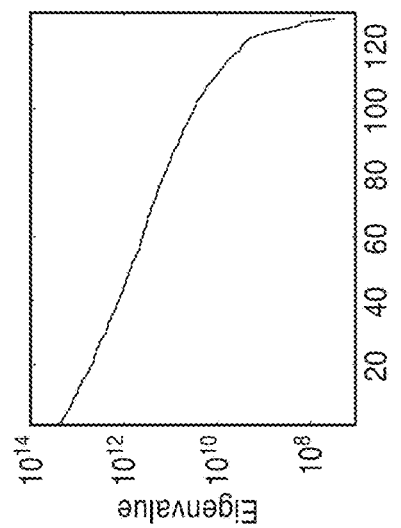

FIG. 15C is a plot of the eigenvalues of the TR matrix.

Figure 16A:
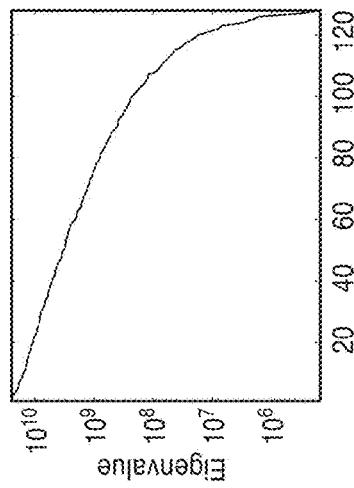

FIG. 16A is a plot of scatterer distribution of a 5 mm×5 mm sub-region.

Figure 16B:
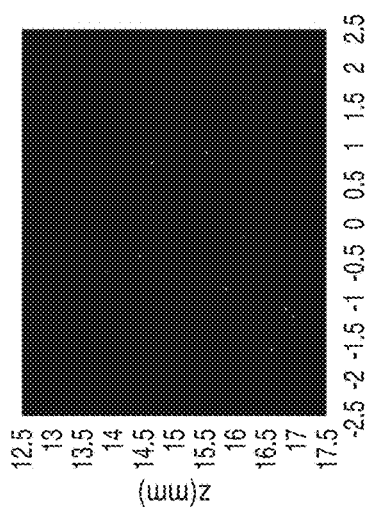
Figure 16C:
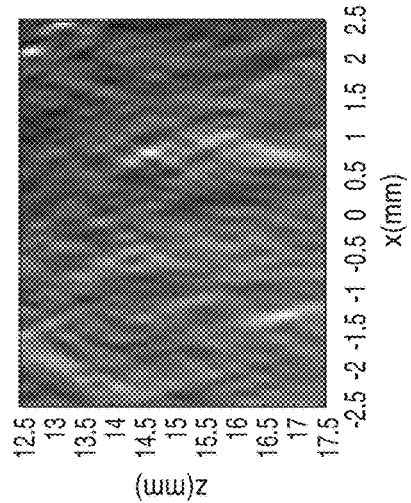

FIG. 16B is a plot of eigenvalues of the TR matrix corresponding to the 5 mm×5 mm sub-region FIG. 16C is an image obtained using 20 eigenvectors with the lowest eigenvalues.

Figure 16D:
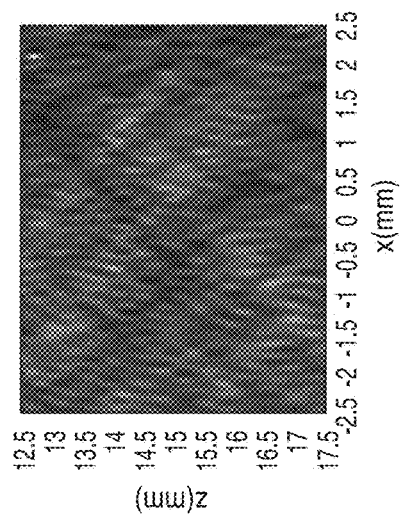

FIG. 16D is an image obtained using a 100 eigenvectors with the lowest eigenvalues.

Figure 17A:
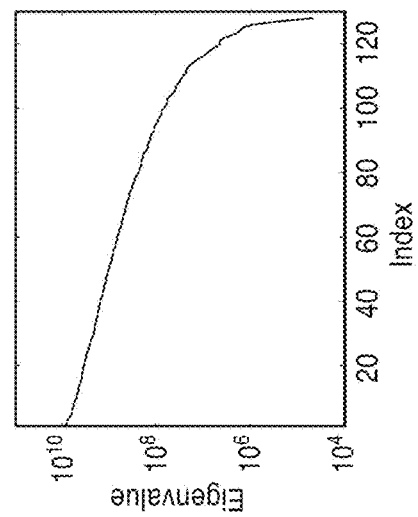

FIG. 17A is an image showing scatterer distribution of a 1 mm×1 mm sub-region.

Figure 17B:
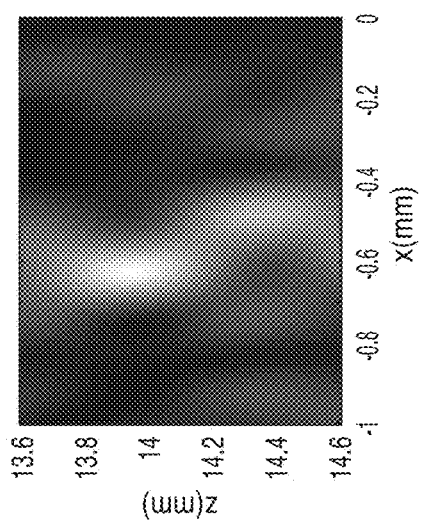

FIG. 17B shows eigenvalues of the TR matrix corresponding to the 1 mm×1 mm sub-region.

Figure 17C:
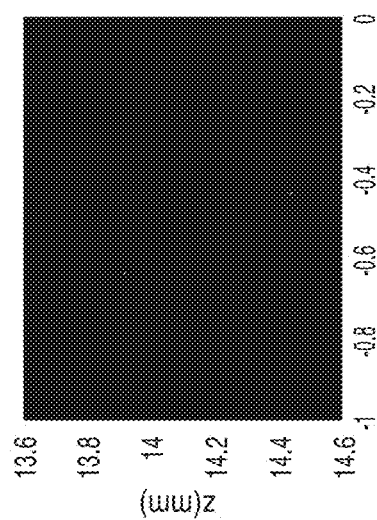

FIG. 17C shows an image obtained using 20 eigenvectors with the lowest eigenvalues.

Figure 17D:
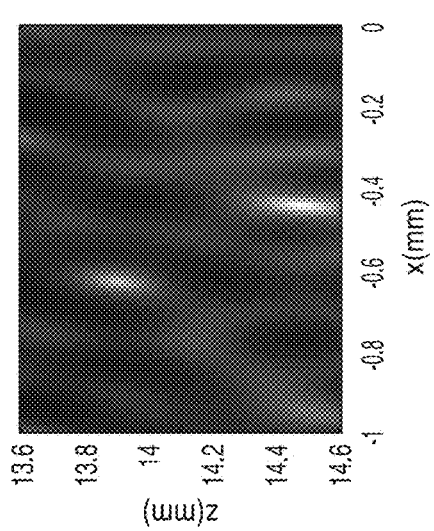

FIG. 17D shows an image obtained using a 100 eigenvectors with lowest eigenvalues.

FIG. 18A shows simulation geometry for 1000 randomly distributed scatterers.

FIG. 18B shows the total image obtained from combining images of 1 mm×1 mm sub-regions.

FIG. 18C shows scatterer distribution of a magnified region close the transducer array.

FIG. 18D shows the corresponding image of the distribution of FIG. 18C.

Figure 18F:
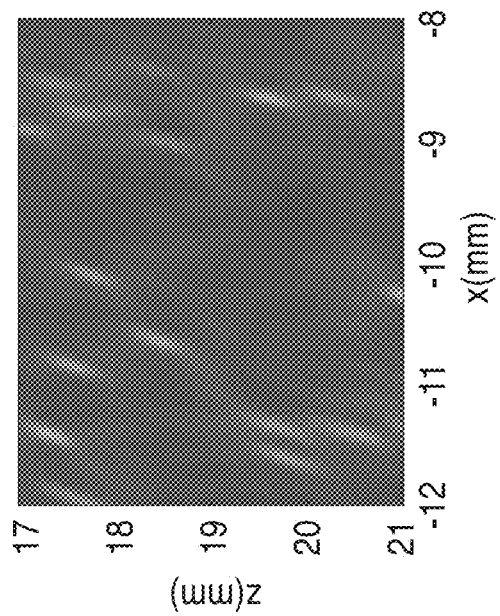
Figure 18E:
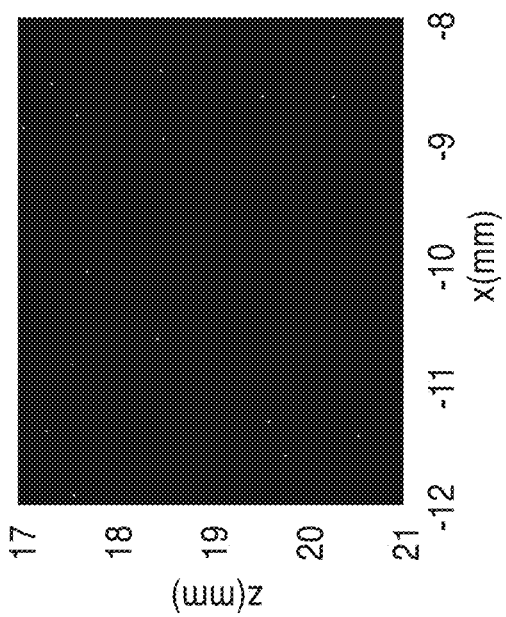

FIG. 18E shows the scatterer distribution of a magnified region far from the transducer array FIG. 18F shows the corresponding image of the distribution of FIG. 18D.

Figure 19A:
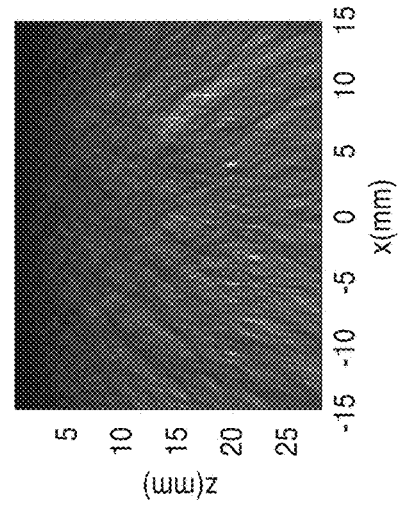
Figure 19B:
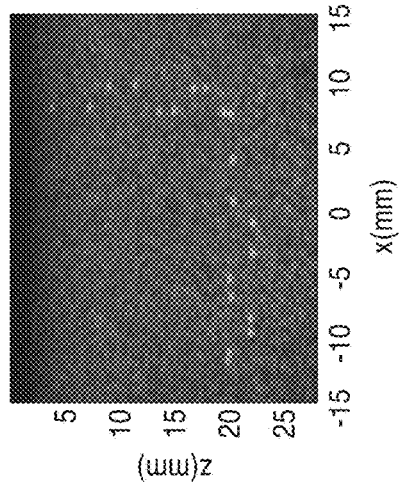
Figure 19C:
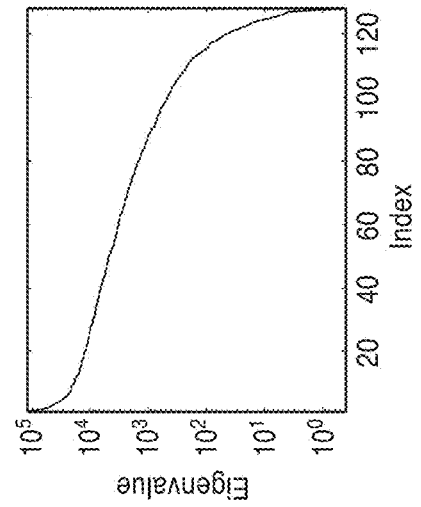

FIG. 19A shows an image of the ATS phantom obtained using the synthetic aperture sultrasound system. FIG. 19B shows the image obtained using the TR-MUSIC algorithm when time windowing is not used. FIG. 19C shows the eigenvalues of the TR matrix.

Figure 20B:
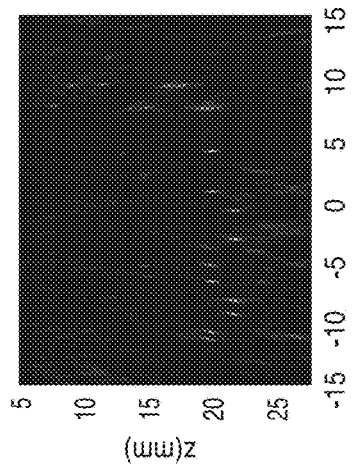
Figure 20D:
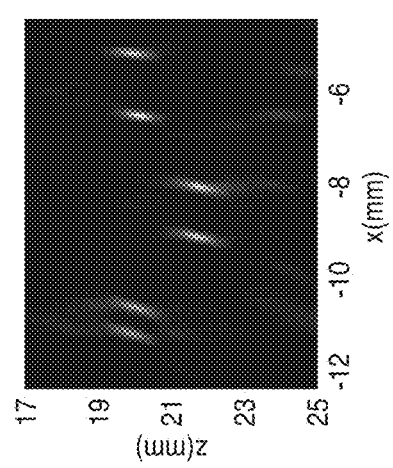
Figure 20A:
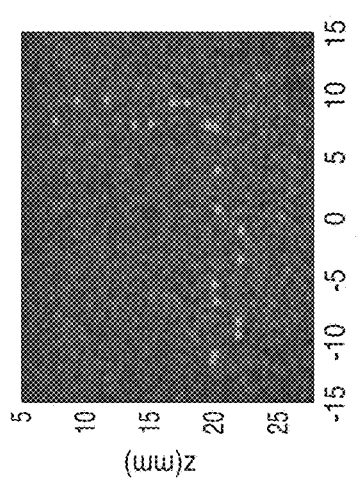
Figure 20C:
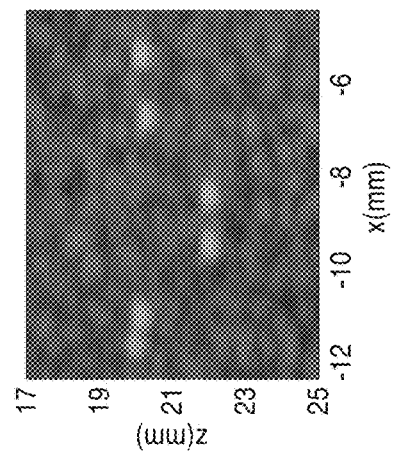

FIG. 20A shows an image of the ATS phantom obtained using the synthetic aperture ultrasound system. FIG. 20B shows the image obtained using the TR-MUSIC algorithm by combining images of 5 mm×5 mm sub-regions. FIG. 20C shows a magnified region of FIG. 20A showing filaments separated laterally. FIG. 20E shows a magnified region of FIG. 20A showing filaments separated axially. FIG. 20D shows a magnified region of FIG. 20B showing filaments separated axially. FIG. 20F shows a magnified region of FIG. 20B showing filaments separated axially.

Figure 21:
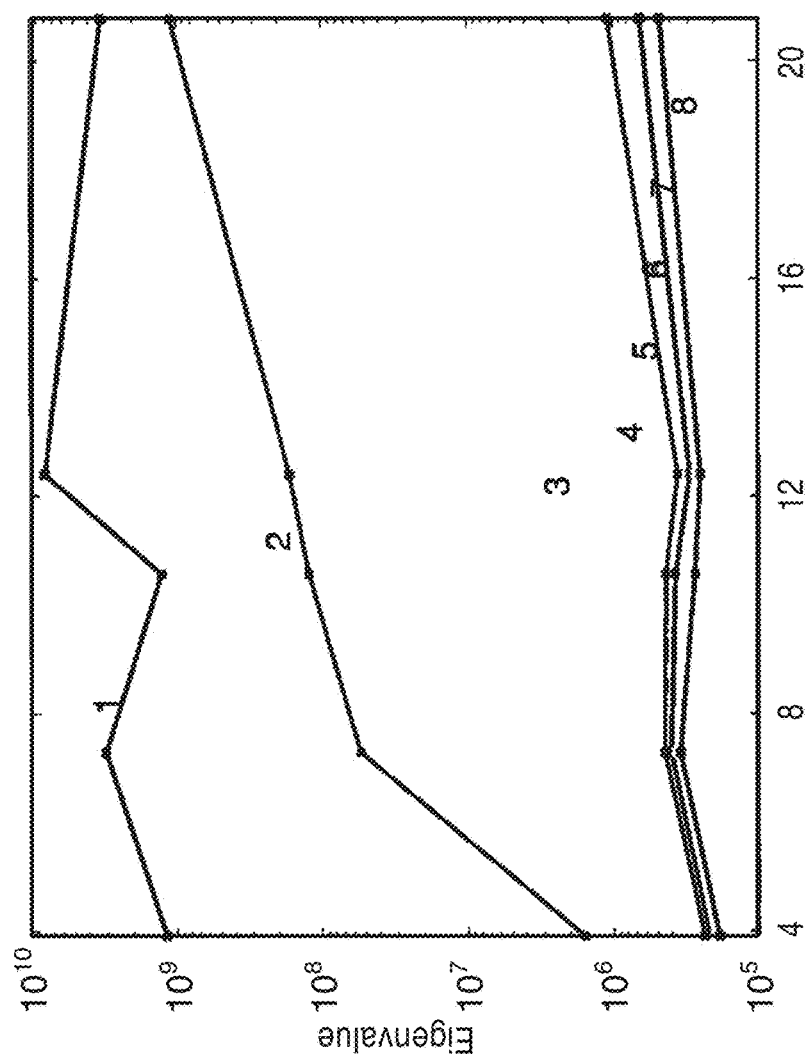
Figure 22B:
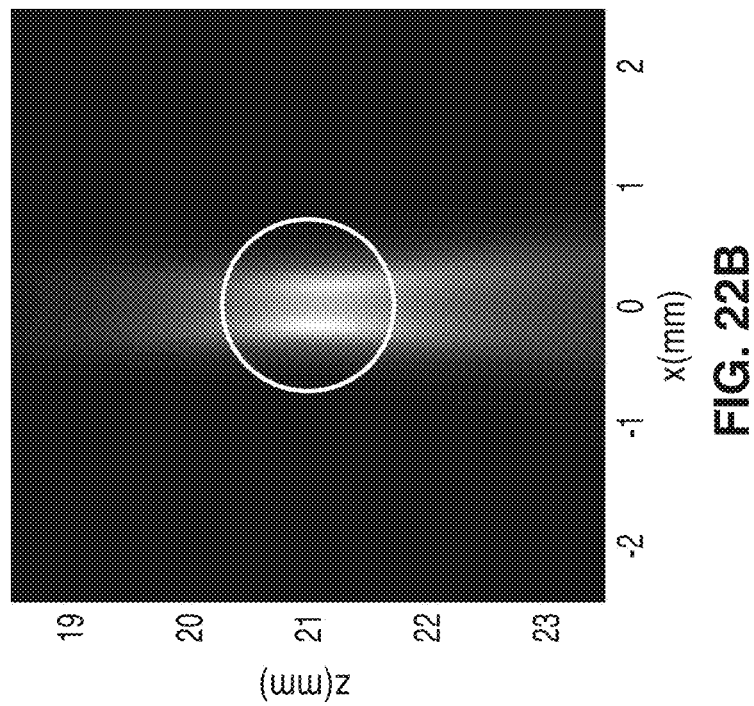
Figure 22A:
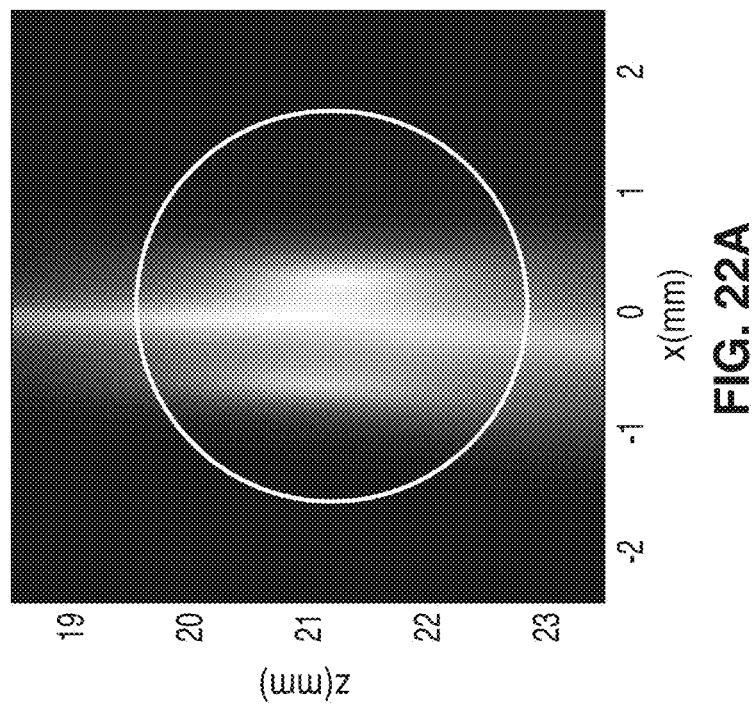
Figure 22D:
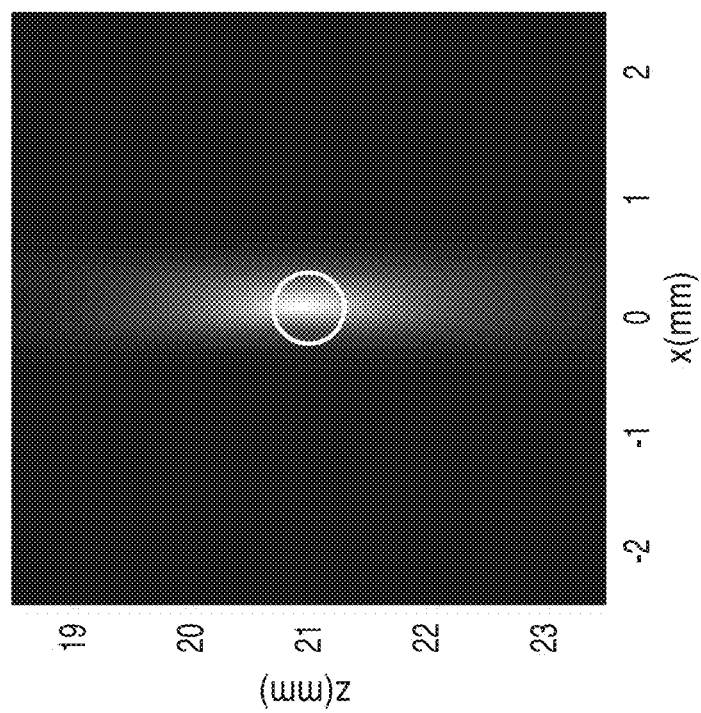
Figure 22C:
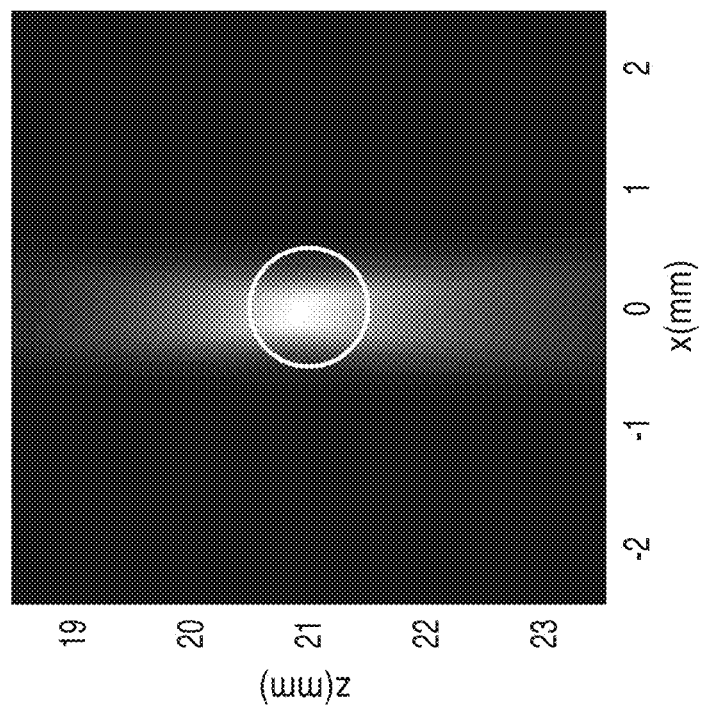

FIG. 21 is a plot of tissue-mimicking phantoms (TMPs) experiment showing the first eight eigenvalues of the TR matrices of the spheres in a versus ka (wavenumber times sphere radius). The glass spheres have a diameter of 2:9 mm, 1:8 mm, 1:5 mm, 1 mm, and 0:55 mm corresponding to ka values of 20.8, 12.4, 10.5, and 7.3, respectively.

FIGS. 22A through 22D show TR-MUSIC images of glass spheres with a diameter of (a) 2:9 mm, (b) 1:5 mm, (c) 1 mm, and (d) 0:55 mm. The white circles show the true sizes of the spheres.

FIGS. 23A through 23D show images of a second phantom obtained using (a) X-ray mammography, (b) synthetic-aperture ultrasound imaging, (c) TR-MUSIC imaging, and (d) TR-MUSIC imaging using 5 mm×5 mm overlapped sub-regions. The spheres of the second phantom have a diameter ranging from 0.25 to 0.3 mm.

FIGS. 24A through 24D show images of a third phantom obtained using (a) X-ray mammography, (b) synthetic-aperture ultrasound imaging, (c) TR-MUSIC imaging, and (d) TR-MUSIC imaging using 5 mm×5 mm overlapped sub-regions. The spheres of the third phantom have a diameter ranging from 0.5 to 0.6 mm.

FIGS. 25A through 25D show images of a fourth phantom obtained using (a) X-ray mammography, (b) synthetic-aperture ultrasound imaging, (c) TR-MUSIC imaging, and (d) Windowed TR-MUSIC imaging using 5 mm×5 mm overlapped sub-regions. The spheres of the fourth phantom have a diameter ranging from 0.8 to 1.2 mm.

DETAILED DESCRIPTION OF THE INVENTION

Figure 1:
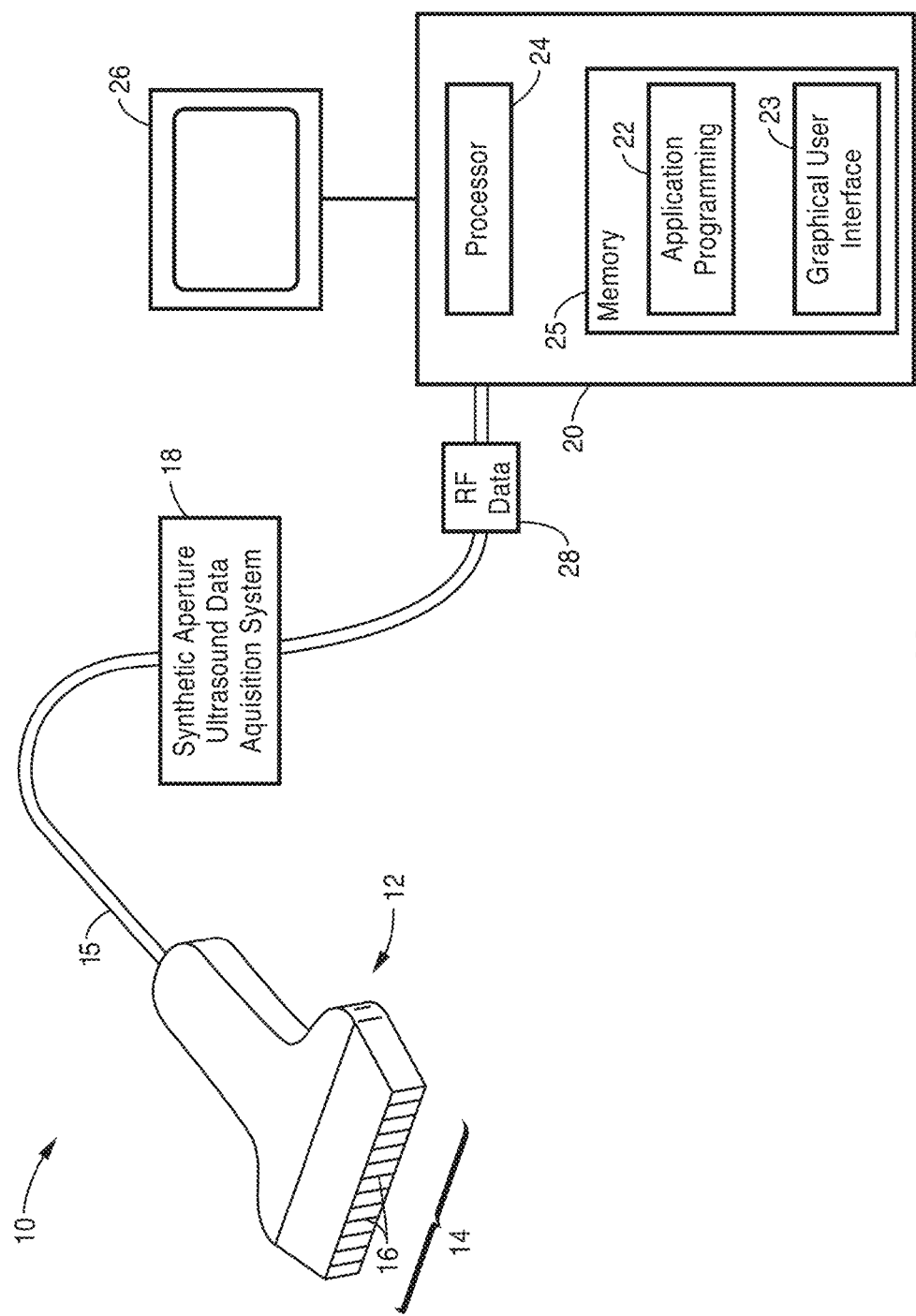
FIG. 1 is a schematic diagram of a synthetic-aperture ultrasound system in accordance with the present invention.

FIG. 1 is a schematic diagram of a synthetic-aperture ultrasound system 10 in accordance with the present invention. The system 10 includes a scanner 12 comprising a plurality of individual transducer elements 16 disposed within a linear array 14. The scanner 12 is coupled to a server or like computing apparatus 20 (e.g. with a cable 15 or other connection means such as, but not limited to, a wireless connections means) and synthetic aperture ultrasound data acquisition system 18 that outputs RF data 28 corresponding to readings acquired by the scanner 12.

Computer 20 comprises a processor 24 configured to operate one or more application programs 22 and graphical user interface (GUI) 23 located within memory 25, wherein the application programs 22 may contain one or more algorithms or methods of the present invention for imaging a tissue medium for display via GUI 23 on monitor 26, or other means. For example, the application programming 22 may comprise the programming configured for operating the sequential excitation method 50 shown in FIG. 3, the generalized TR-MUSIC method 66 shown in FIG. 4, and/or the windowed TR-MUSIC method 100 shown in FIG. 6.

Figure 2:
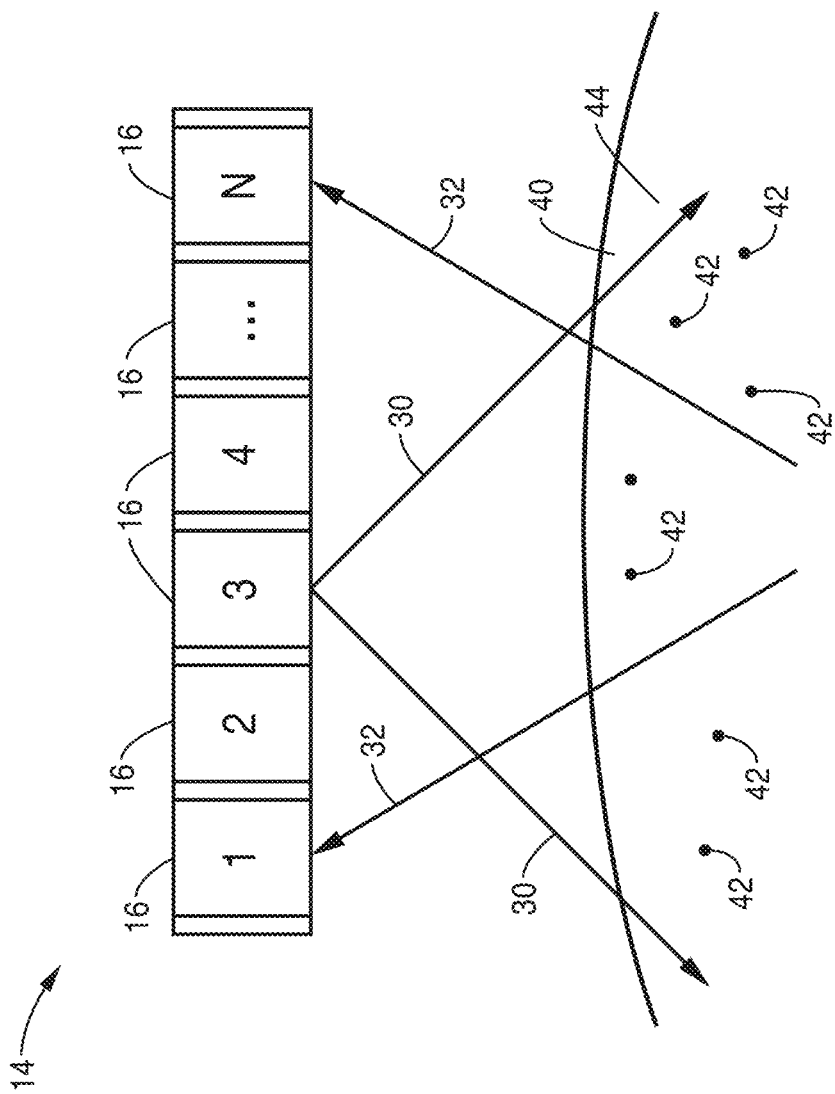
FIG. 2 is a schematic diagram of the scanner of the ultrasound system of FIG. 1 interrogating a region of tissue.

FIG. 2 is a schematic diagram of the array 14 of scanner 12 of the ultrasound system 10 shown in FIG. 1 interrogating a region of tissue 44. In ultrasound imaging applications, TR focusing uses an array 14 of N transducers 16 acting in the transmit-receive mode.

Each element of the array 14 is excited sequentially (e.g. transducer 3 is shown in excitation mode) to generate an ultrasound field or signal 30 through the tissue surface 40 and into tissue region 44. The backscattered signals 32 are measured in parallel by all N elements 16, yielding the inter-element response matrix K($\omega$) of the array at the angular frequency $\omega$. The matrix K($\omega$) is then used to compute the TR matrix T($\omega$)=K*($\omega$)K($\omega$). When the interrogated medium contains M well-resolved point scatterers 42, such that M<N, the TR operator has M eigenvectors with nonzero eigenvalues, and these eigenvectors correspond one-to-one with the different point scatterers 42.

Focusing on a single scatterer 42 can be achieved experimentally by using all elements 16 of the array 14 to back-propagate the eigenvector associated with that scatterer 42. If the geometry of the array 14 and the Green's function of the medium 44 are known, backpropagation can be computed numerically to obtain images of the different scatterers 44. The use of MUSIC with the TR operator yields a pseudo-spectrum that peaks at the locations of the point scatterers 44. This algorithm produces high-resolution images of point scatterers, even when the scatterers 44 are not well resolved by the imaging system.

Figure 3:
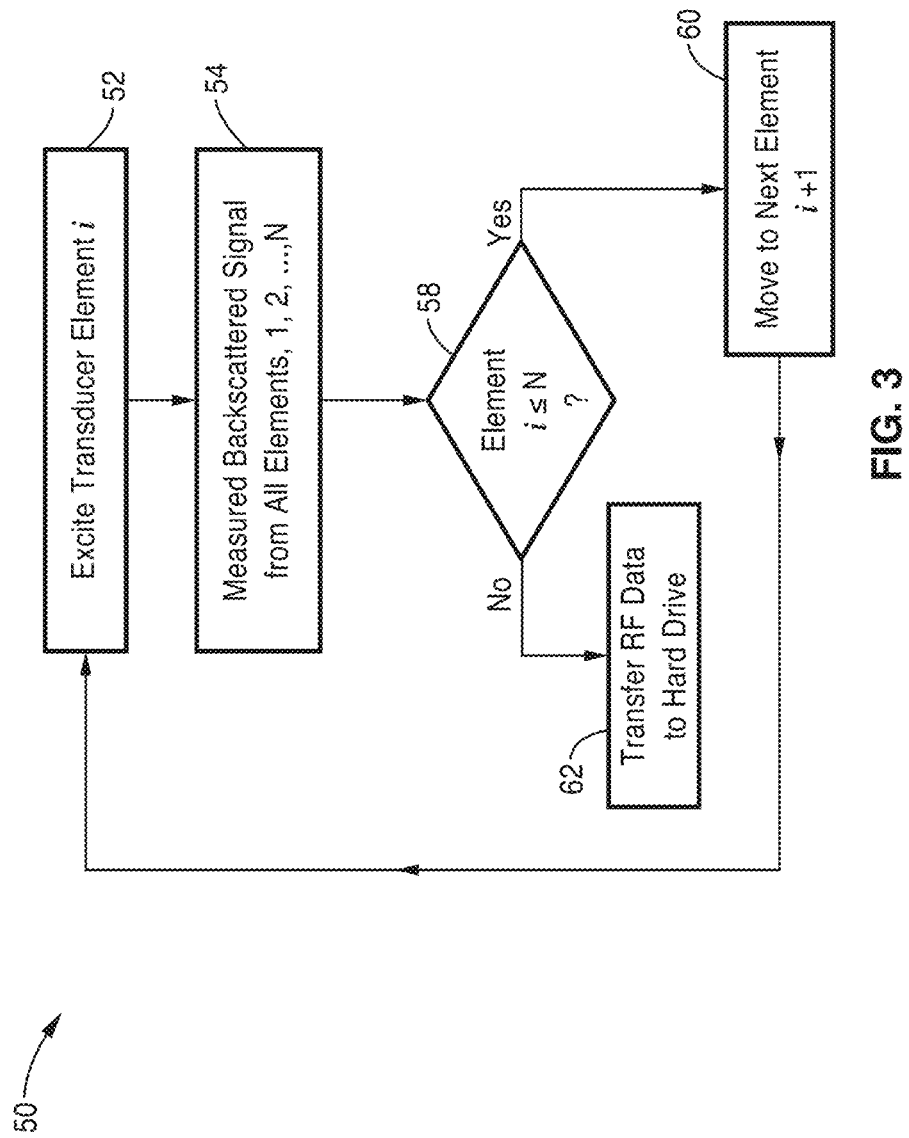
FIG. 3 shows a flow diagram of a method for sequentially exciting a region of tissue in accordance with the present invention.

FIG. 3 shows flow diagram of a method 50 for sequentially exciting a region of tissue 44 in accordance with the present invention. At step 52, a first element (e.g. element 1 or i) of array 14 of N ultrasound transducer elements 16 is excited for interrogating an inhomogeneous medium 42. At step 54, the backscattered signals are measured by all elements 16 in the array 14. At step 58, the method evaluates whether all the elements 16 in the array 14 have been excited (and imaged). If the last element in the array 14 has not been reached, the method moves to the next element 16 in the array 14 at step 60, and repeats the process sequentially until the $N^{th}$ element is reached at step 62. At this point, the process 50 transfers the RF data to memory 25.

Generalized TR-MUSIC Algorithm

Figure 4:
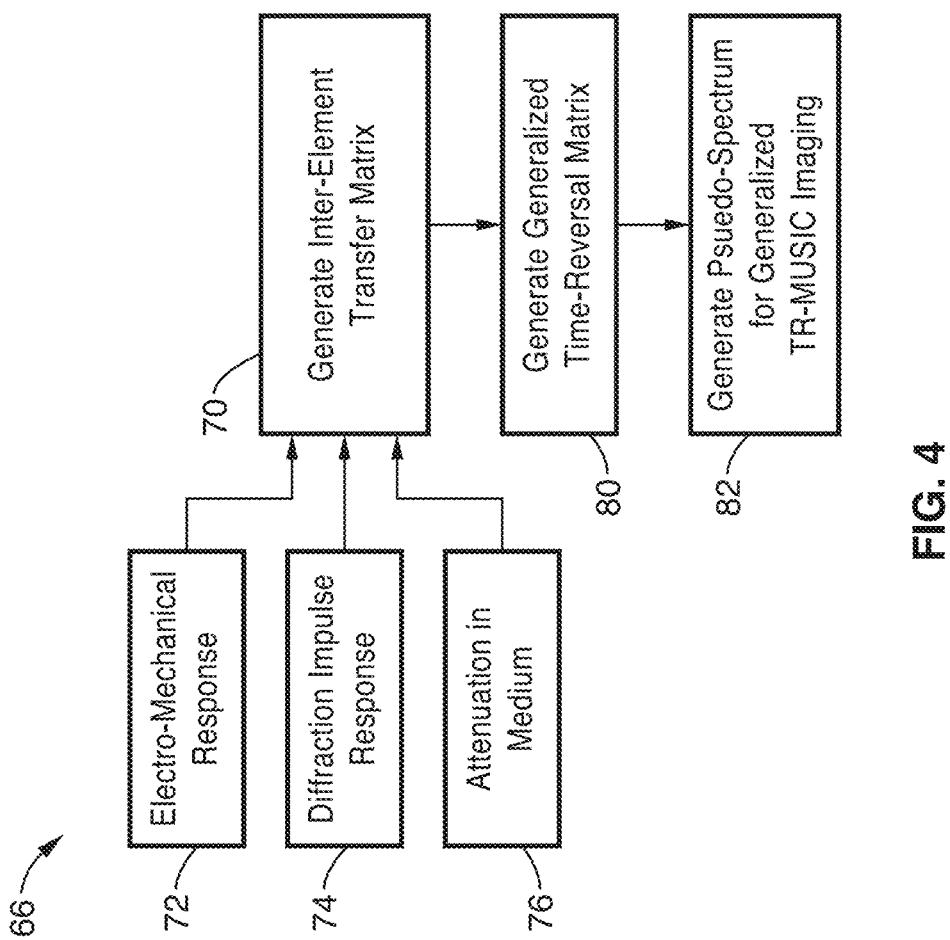
FIG. 4 is a flow diagram of the generalized TR-MUSIC method of the present invention.

FIG. 4 shows a flow diagram of the generalized TR-MUSIC method 66 of the present invention. In a preferred embodiment, the method 66 generates an inter-element transfer matrix at step 70, which incorporates the electromechanical response 72 of each element 16 in the array 14, the diffraction impulse response 74 of each element 16, and the attenuation in the medium 76. Next, at step 80, the generalized time-reversal (TR) matrix is generated. Finally, a pseudo-spectrum for generalized TR-Music imaging is generated at step 82. Each of these steps will be described in further detail below.

The derivation of the expression for the matrix K is detailed as follows. First, the equation for the scattered field from an inhomogeneous medium is presented. Then, the transducer model is considered for calculation of the incident field. Finally, the wave-equation solution and the transducer model are combined to give the equation for the recorded electrical signal and form each element of the inter-element response matrix $K_{ij}(\omega)$.

The integral equation for the scattered pressure field from an inhomogeneous medium is given by Eq. 1:

$$p_s(r, \omega) = \iiint_{V_0} \{k^2 \gamma_\kappa(r_0) p(r_0, \omega) g_0(\omega, r | r_0) - \nabla \cdot [\gamma_\rho(r_0) \nabla p(r_0, \omega)] g_0(r | r_0, \omega)\} dv_0 \quad \text{Eq. 1}$$

where $\omega$ is the angular frequency and $V_0$ is the scattering volume. The fluctuation functions $\gamma_\kappa$ and $\gamma_\rho$ are measures of the relative compressibility and density differences between the scatterer and the surrounding medium given by:

$$\gamma_\kappa(r) = \frac{\kappa(r) - \kappa_0}{\kappa_0}, \quad \text{Eq. 2}$$

$$\gamma_\rho(r) = \frac{\rho(r) - \rho_0}{\rho(r)}, \quad \text{Eq. 3}$$

where $\rho_0$ is the average density, and $\kappa_0$ is the average compressibility of the medium. The complex wave number k is:

$$\underline{k} = \frac{\omega}{c} - i\alpha, \quad \text{Eq. 4}$$

where $k=\omega/c$ is the real wave number, $\alpha$ is the amplitude attenuation coefficient, c is the average sound speed, and i is the imaginary unit. The free-space Green's function $g_0(\omega, r|r_0)$ is given by:

$$g_0(\omega, r | r_0) = \frac{\exp(-i\underline{k}|r - r_0|)}{4\pi |r - r_0|}. \quad \text{Eq. 5}$$

Because the wavenumber k of Eq. 4 is complex, the Green's function accounts for the attenuation in the medium shown in step 76 of FIG. 4.

In the following, the transducer model is used to derive the equation for the ultrasound incident field.

The ultrasound incident field is generated by an ultrasound transducer element 16, assuming no other sources exist in the medium 44. In the classical theory of sound in a fluid that exhibits viscous loss, the pressure phasor is given by:

$$p_{inc}(r, \omega) = \frac{i\underline{k}^2 \Phi(r, \omega)}{\omega \kappa_0}, \quad \text{Eq. 6}$$

where $\Phi(r,\omega)$ is the velocity potential. For a planar transmitting transducer element 16 of area S, the velocity potential is:

$$\Phi(r,\omega) = V_n(\omega) H(r,\omega), \quad \text{Eq. 7}$$

where $V_n(\omega)$ is the particle velocity normal to the surface of the transducer element, and $H(r,\omega)$ is the diffraction impulse response generated at step 74 of FIG. 4, and also may be referred to as the velocity-potential impulse response. The particle velocity and the diffraction impulse response are given, respectively, by:

$$V_n(\omega) = W_t(\omega) E(\omega), \quad \text{Eq. 8}$$

and $$H(r, \omega) = \iint_{S_t} \frac{\exp(-i\underline{k}|r - r_0|)}{2\pi |r - r_0|} ds_0, \quad \text{Eq. 9}$$

where the integral is evaluated over the surface of the transmitting element $S_t$, $W_t(\omega)$ is the transmitter electromechanical transfer function, and $E(\omega)$ is the input-voltage transfer function. In Eq. 9, it is assumed that the acoustic velocity distribution is constant over the area $S_t$. Using the previous four equations, the incident pressure field is given by:

$$p_{inc}(r, \omega) = \frac{i\underline{k}^2}{\omega \kappa_0} W_t(\omega) E(\omega) \iint_{S_t} \frac{\exp(-i\underline{k}|r - r_0|)}{2\pi |r - r_0|} ds_0. \quad \text{Eq. 10}$$

The spectrum of the electrical signal measured by the receiving transducer element is given by:

$$p_m(\omega) = W_r(\omega) \iint_{S_r} p_s(r, \omega) ds, \qquad \text{Eq. 11}$$

where the integral is evaluated over the receiving-element area $S_r$, and $W_r(\omega)$ is the receiver electro-mechanical transfer function. In Eq. 11, it is assumed that the spatial sensitivity of the scanner/detector 12 is constant across the area $S_r$. Using this assumption, the sensitivity of the detector 12 is incorporated into $W_r(\omega)$. When the magnitudes of $\gamma_\rho$ and $\gamma_\kappa$ are small, the Born approximation is valid and the scattered wave from Eq. 1 becomes:

$$p_s(r, \omega) = \iiint_{V_0} \{k^2 \gamma_\kappa(r_0) p_{inc}(r_0, \omega) g_0(r \mid r_0, \omega) - \qquad \text{Eq. 12}$$
$$\nabla \cdot [\gamma_\rho(r_0) \nabla p_{inc}(r_0, \omega)] g_0(r \mid r_0)\} dv_0$$

where the pressure field $p(r,\omega)$ is replaced by the incident field $p_{inc}(r,\omega)$ on the right-hand side of Eq. 1. By substituting Eq. 12 and assuming that the scatterers are sufficiently far from the transducer element 16, such that $|r-r_0| \gg \lambda$ where $\lambda$ is the ultrasound wavelength, Eq. 13 is obtained:

$$p_s(r, \omega) = \frac{2ik^4}{\omega \kappa_0} W_t(\omega) E(\omega) \iiint_{V_0} \qquad \text{Eq. 13}$$
$$\left\{ [\gamma_\kappa(r_0) + \cos(\theta) \gamma_\rho(r_0)] g_0(r \mid r_0) \times \iint_{S_t} g_0(r_0 \mid r') ds' \right\} dv_0,$$

where $\theta$ is the angle between the vector from the center of the transmitting element 16 to the point where the inhomogeneity is located, and the vector from the location of the inhomogeneity to the observation point.

Substituting Eq. 11 yields Eq. 14:

$$p_m(\omega) = \qquad \text{Eq. 14}$$
$$\frac{2ik^4}{\omega \kappa_0} W_t(\omega) E(\omega) W_r(\omega) \iiint_{V_0} \left\{ [\gamma_\kappa(r_0) + \cos(\theta) \gamma_\rho(r_0)] \iint_{S_t} \right.$$
$$\left. g_0(r_0 \mid r', \omega) ds' \iint_{S_r} g_0(r \mid r_0, \omega) ds \right\} dv_0$$

It is assumed that density fluctuations are much smaller than compressibility fluctuations. Therefore, Eq. 14 can be simplified as:

$$p_{i,j}(\omega) = \frac{2ik^4}{\omega \kappa_0} E(\omega) F_{i,j}(\omega) \iiint_{V_0} \gamma_\kappa(r_0) a_i(r_0, \omega) a_j(r_0, \omega) dv_0, \qquad \text{Eq. 15}$$

where the subscript i denotes the transmitting element, the subscript j denotes the receiving element, $a_i(r_0,\omega)$ is the integral of the Green's function over the surface of element i given by:

$$a_i(r_0, \omega) = \iint_{S_i} g_0(r \mid r_0) ds, \qquad \text{Eq. 16}$$

and the electromechanical transfer function $F_{i,j}(\omega)$ is given by:

$$F_{i,j}(\omega) = W_{t_i}(\omega) W_{r_j}(\omega). \qquad \text{Eq. 17}$$

The integration in Eq. 16 accounts for the finite size effects of the ultrasound transducer elements 16 used in the derivation of the inter-element transfer matrix of step 70 in FIG. 4.

Figure 5:
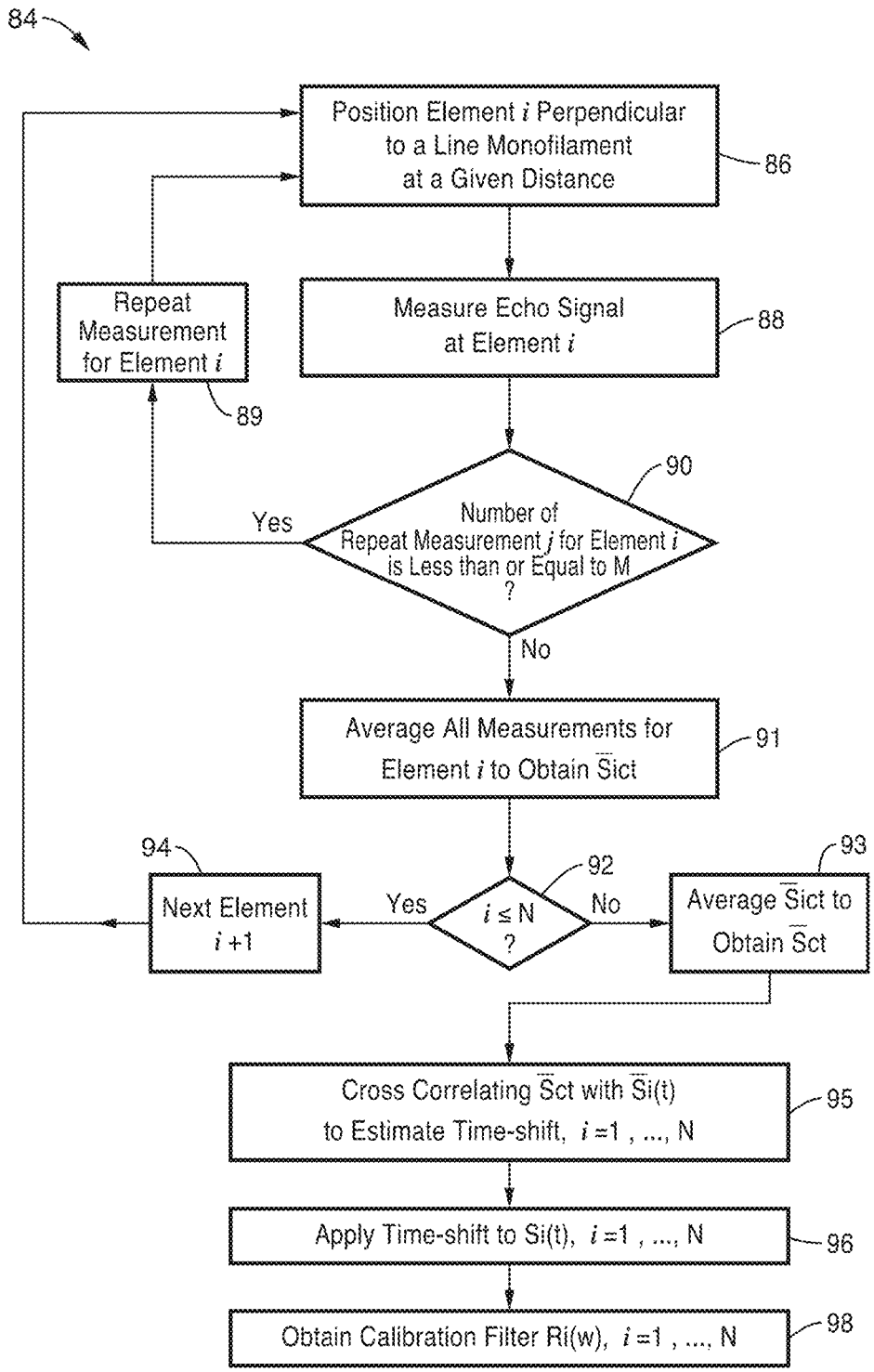
FIG. 5 shows a flow diagram for a calibration method to compensate for the electro-mechanical response (time response) of ultrasound transducer elements, and their variations in the element-to-element sensitivity.

With respect to the electro-mechanical parameters 72 of FIG. 4, variations in the sensitivity and time response from element-to-element may be compensated by calibration. FIG. 5 shows a flow diagram for a calibration method 84 that compensates for the electro-mechanical response (time response) 72 of ultrasound transducer elements 16, and their variations in the element-to-element sensitivity. Method 84 is a preferred method for calibrating a linear transducer array 24. However it is appreciated that other methods available in the art may be employed.

Referring to FIG. 5, the first step in the calibration method 84 is to position element i perpendicular and at a specified distance from a target line filament at step 86. Next, element i transmits and receives an echo from the target at step 88. This pulse-echo experiment is repeated M (e.g. 10) times at step 89 for each of the 128 elements. If the number of repeat measurements for element i reaches M iterations at step 90, the averaged RF waveform $s_i(t)$ is obtained by averaging all M measurements for i at step 91. At step 92, an evaluation is made to determine if all N elements have been excited. If not, the above steps are repeated at step 94. If all elements have been excited, a reference waveform $\bar{s}(t)$ is obtained at step 93 by averaging all 128 waveforms. Due to small variations in the position of the monofilament with respect to the center of the elements, a time-shift correction for each element 16 is obtained by cross-correlation of the echo signal $s_i(t)$ with $\bar{s}(t)$ at step 95. At step 96, the time-shift correction is applied to $s_i(t)$ obtained for each element. The reference waveform is used with the time-aligned echo signal $s_i(t)$ to compute the compensation filter $r_i(t)$ that matches the echo signal $s_i(t)$ with the reference waveform $\bar{s}(t)$ to obtain the calibration filter $Ri(\omega)$ at step 98.

An exemplary calibration for a transducer array was performed using the method 84, and is described in further detail below. Integration of this calibration data into the inter-element response matrix is explained as follows. The calibrated spectrum $p_{i,j}^{cal}(\omega)$ is given by Eq. 18:

$$p_{i,j}^{cal}(\omega) = R_i(\omega) R_j(\omega) p_{i,j}(\omega) = \qquad \text{Eq. 18}$$
$$\frac{2ik^4}{\omega \kappa_0} E(\omega) R_i(\omega) R_j(\omega) F_{i,j}(\omega) \iiint_{V_0} \gamma_{\kappa(r_0)} a_i(r_0) a_j(r_0) dv_0 =$$
$$\frac{2ik^4}{\omega \kappa_0} E(\omega) F(\omega) \iiint_{V_0} \gamma_\kappa(r_0) a_i(r_0) a_j(r_0) dv_0$$

where $p_{i,j}(\omega)$ is the spectrum given by Eq. 15 and $R_i(\omega)$ and $R_j(\omega)$ are the calibration filters for elements i and j, respectively. The function $F(\omega) = R_i(\omega) R_j(\omega) F_{i,j}(\omega)$ is now independent of the subscripts i and j. Using Eq. 18 the inter-element response matrix K is given by Eq. 19:

$$K = \frac{2ik^4}{\omega\kappa_0} F(\omega) \int \int \int_{V_0} \gamma_\kappa(r_0) A_{r_0} A_{r_0}^T dv_0, \qquad \text{Eq. 19}$$

where the superscript T denotes the transpose and $A_{r_0}$ is an N-dimensional column vector given by:

$$[a_1(r_0,\omega) a_2(r_0,\omega) \ldots a_N(r_0,\omega)]. \qquad \text{Eq. 20}$$

The expression for the inter-element transfer matrix given by Eq. 19 is used in step 70 shown in FIG. 4, and is more general than that previously derived by other investigators. The generalized expression used in accordance with the present invention incorporates attenuation of the medium, diffraction effects caused by the finite size of the transducer elements, and the sensitivity and time response of the elements.

The behavior of the TR-MUSIC algorithm depends on the coherent point spread function (CPSF) of the ultrasound imaging system. An expression for the CPSF of a linear ultrasound array of N elements is derived. The inter-element transfer matrix K is then used to derive an equation for the time-reversal matrix T at step 80 (see FIG. 4). The matrix T is then used to derive a generalized expression for the pseudo-spectrum 82 for the generalized TR-MUSIC algorithm 66 of the present invention.

In classical TR imaging, images are formed by back-propagating the waves measured by all elements 16 of the transducer array 14. The backpropagation is performed numerically, assuming the sound speed and the transducer-array 14 geometry are known. The CPSF of a transducer array 14 is the image of a point source obtained using classical TR imaging. The CPSF plays an important role in connection with the lateral and axial resolutions of the TR-MUSIC algorithm. In the following, an equation for the CPSF is derived.

The wavefield at location r that results from a point source at $r_0$ is given by the Green's function $g(r|r_0,\omega)$. Using Eq. 11, the signal measured by element i is:

$$p_i(\omega) = W_r(\omega) \int\int_{S_r} g_0(r|r_0,\omega) ds = W_{ri}(\omega) a_i(\omega, r_0), \qquad \text{Eq. 21}$$

where the term $p_s(r,\omega)$ is replaced by $g_0(r|r_0,\omega)$ in Eq. 11. By simultaneously re-emitting the time-reversed measured signals from each transducer element, ultrasound waves are focused back to the location of the point source. In the frequency domain, this operation is equivalent to re-emitting the complex conjugates of the spectra of the measured signals. The CPSF is the sum of the re-emitted fields. Using Eq. 10 and Eq. 21, the CPSF equation Eq. 22 is obtained:

$$CPSF(r|r_0,\omega) = \frac{2ik^2}{\omega\kappa_0} \sum_{i=1}^{N} W_{ti}(\omega)[W_{ri}(\omega)a_i(r_0,\omega)]^* a_i(r,\omega) \qquad \text{Eq. 22}$$

$$= \frac{2ik^2}{\omega\kappa_0} \sum_{i=1}^{N} W_{ri}^*(\omega) W_{ti}(\omega) a_i^*(r_0,\omega) a_i(r,\omega)$$

where $E_i(\omega)$ is replaced by $p^*_i(\omega)$ in Eq. 10 and sum over the number of transducer elements 16. An approximate expression for the CPSF is obtained by assuming that the transmit and receive electromechanical responses are equal for all array elements, i.e., $W_{ti}(\omega) = W_t(\omega)$ and $W_{ri}(\omega) = W_r(\omega)$. Therefore, the CPSF is given by:

$$CPSF(r|r_0,\omega) = W_r^*(\omega) W_t(\omega) \sum_{i=1}^{N} a_i^*(r_0,\omega) a_i(r,\omega) \qquad \text{Eq. 23}$$

$$= W_r^*(\omega) W_t(\omega) \langle A_{r_0}, A_r \rangle$$

where the angular brackets denote the inner product in $C^N$, i.e., $$\langle A_{r_0}, A_r \rangle = A_{r_0}^\dagger \cdot A_r = \sum_{i=1}^{N} a_i^*(r_0,\omega) a_i(r,\omega) \qquad \text{Eq. 24}$$

The superscript † denotes the conjugate transpose. The CPSF achieves a maximum at the location of a point source, and decays away from the point source. The spatial extent of the CPSF is determined by the size of the elements, the number of elements, the geometry of the transducer array, the location of the point source with respect to the transducer array, and the ultrasound wavelength. Based on this result, two point scatterers located at $r_m$ and $r_{m'}$ are well resolved by the imaging system only if:

$$\langle A_{r_{m'}}, A_{r_m} \rangle = \langle A_{r_{m'}}, A_{r_m} \rangle \delta_{m,m'}, \qquad \text{Eq. 25}$$

where $\delta$ is the delta function.

The time-reversal matrix T is defined as:

$$T = K^\dagger K = K^* K, \qquad \text{Eq. 26}$$

where the superscripts † and * denote the adjoint and the complex-conjugate of the matrix, respectively. The second equality follows from the fact that the inter-element transfer matrix K is symmetric. Applying Eq. 19 results in:

$$T = \frac{-4k^8}{(\omega\kappa_0)^2} |F(\omega)|^2 \int\int\int_{V_0}\int\int\int_{V_0} [\Lambda(r_0, r'_0) A_{r_0}^* A_{r'_0}^T] dv_0 dv'_0, \qquad \text{Eq. 27}$$

where $$\Lambda(r_0, r'_0) = \gamma_\kappa(r_0) \gamma_\kappa(r'_0) \langle A_{r_0}, A_{r'_0} \rangle. \qquad \text{Eq. 28}$$

The TR matrix is self-adjoint because:

$$T^\dagger = [(K^*K)^*]^T = (KK^*)^T = (K^\dagger K^T) = (K^*K) = T, \qquad \text{Eq. 29}$$

and positive semi-definite because for any vector v, we have:

$$\langle Tv, v \rangle = \langle K^*Kv, v \rangle = \langle Kv, Kv \rangle = \|Kv\|^2 \geq 0. \qquad \text{Eq. 30}$$

It is observed that a positive semi-definite matrix has N non-negative eigenvalues. Indeed if $Tv = \lambda v$ then $\langle Tv, v \rangle = \lambda \|v\|^2 \geq 0$ yielding $\lambda \geq 0$. The eigenfunction associated with the largest eigenvalue of the matrix T specifies an incident wave that maximizes the scattered energy received by the transducer elements. In other words, transmitting the eigenvector associated with the largest eigenvalue focuses energy on the medium inhomogeneities that would result in the maximum scattered energy received by the transducer elements. Other eigenvectors also focus energy on inhomogeneities with and efficiency that is quantified by the associated eigenvalues. In the special case where the medium contains M point scatterers, Eq. 27 becomes:

$$T = \frac{-4k^8}{(\omega K_0)^2}|F(\omega)|^2\sum_{m=1}^{M}\sum_{m'=1}^{M}\Lambda_{m,m'}A_{r_m}^*A_{r_m}^T,$$  Eq. 31 where $$A_{r_m}^T = [\,a_1(r_m,\omega)\quad a_2(r_m,\omega)\quad \ldots\quad,\quad a_N(r_m,\omega)\,]$$  Eq. 32 and $$\Lambda_{m,m'} = \gamma_\kappa(r_m)\gamma_\kappa(r_m')\langle A_{r_m}, A_{r_m'}\rangle.$$  Eq. 33

Eq. 31 is the generalized TR matrix detailed in step 80 shown in FIG. 4, and accounts for electromechanical response, variations in element sensitivity, attenuation in the target medium, etc. Note that Eq. 31 is a more general expression for the TR matrix than previously derived by other investigators.

When the number of scatterers M is less than the number of transducer element N, the rank of the matrix T is equal to M. Since the matrix T is self-adjoint and positive semi-definite, the matrix has M eigenvectors with positive non-zero eigenvalues, and (N−M) eigenvectors with zero eigenvalues. In addition, all the eigenvectors are orthogonal; i.e., $$T\mu_m = \lambda_m\mu_m \quad m=1,2,\ldots,M$$

$$T\mu_{m_0} = 0 \quad m_0 = M+1, M+2, \ldots, N$$  Eq. 34

$$\langle \mu_m, \mu_{m'}\rangle = \delta_{m,m'},$$

where $\mu_m$ is an eigenvector with nonzero eigenvalue, $\mu_{m_0}$ is an eigenvector with zero eigenvalue, and $\lambda_m$ is a positive eigenvalue. When the scatterers are well resolved, the eigenvectors with non-zero eigenvalues are exactly the vectors $A^*_{r_m}$. When the scatterers are not well resolved by the imaging system, each eigenvector with non-zero eigenvalue is a linear superposition of the vectors $A^*_{r_m}$.

The MUSIC algorithm makes use of the fact that the matrix T is a projection operator into the subspace spanned by the vectors $A^*_{r_m}$. This means that the (N−M) eigenvectors with zero eigenvalues are orthogonal to any linear combination of the vectors $A^*_{r_m}$ i.e., $$\langle \mu_{m_0}, A^*_{r_m}\rangle = \langle \mu^*_{m_0}, A_{r_m}\rangle = 0 \quad m=1,2,\ldots,M \; m_0 = M+1, M+2, \ldots, N.$$

$$m_0 = M+1, M+2, \ldots, N.$$  Eq. 35

The MUSIC algorithm for time-reversal imaging is obtained by forming the pseudo-spectrum PS(r) such that:

$$PS(r) = \frac{1}{\sum_{m_0=M+1}^{N}|\langle \mu^*_{m_0}, A_r\rangle|^2}.$$  Eq. 36

The inner product $\langle \mu^*_{m_0}, A_r\rangle$ will vanish whenever r corresponds to the location of one of the scatterers, and this would occur for well-resolved as well as non-resolved scatterers. Note that under ideal situations when the recorded signals are not corrupted by noise, the pseudo-spectrum will exhibit super-resolution, i.e. the resolution of imaging point scatterers will exceed the resolution dictated by the CPSF. The generalized expression for the pseudo-spectrum (e.g. step 82 in FIG. 4), which is given by Eq. 36 above, accounts for the attenuation in the background medium, and the diffraction effects caused by the finite size of the transducer elements 16.

Windowed TR-MUSIC Algorithm

When the number of scatterers is larger than the number of transducer elements, the eigenvectors of the TR matrix all have nonzero eigenvalues. In this case, the TR-MUSIC imaging algorithm is no longer valid for imaging point scatterers. This problem can also occur if the imaging plane contains numerous extended targets.

Figures 6, 7:
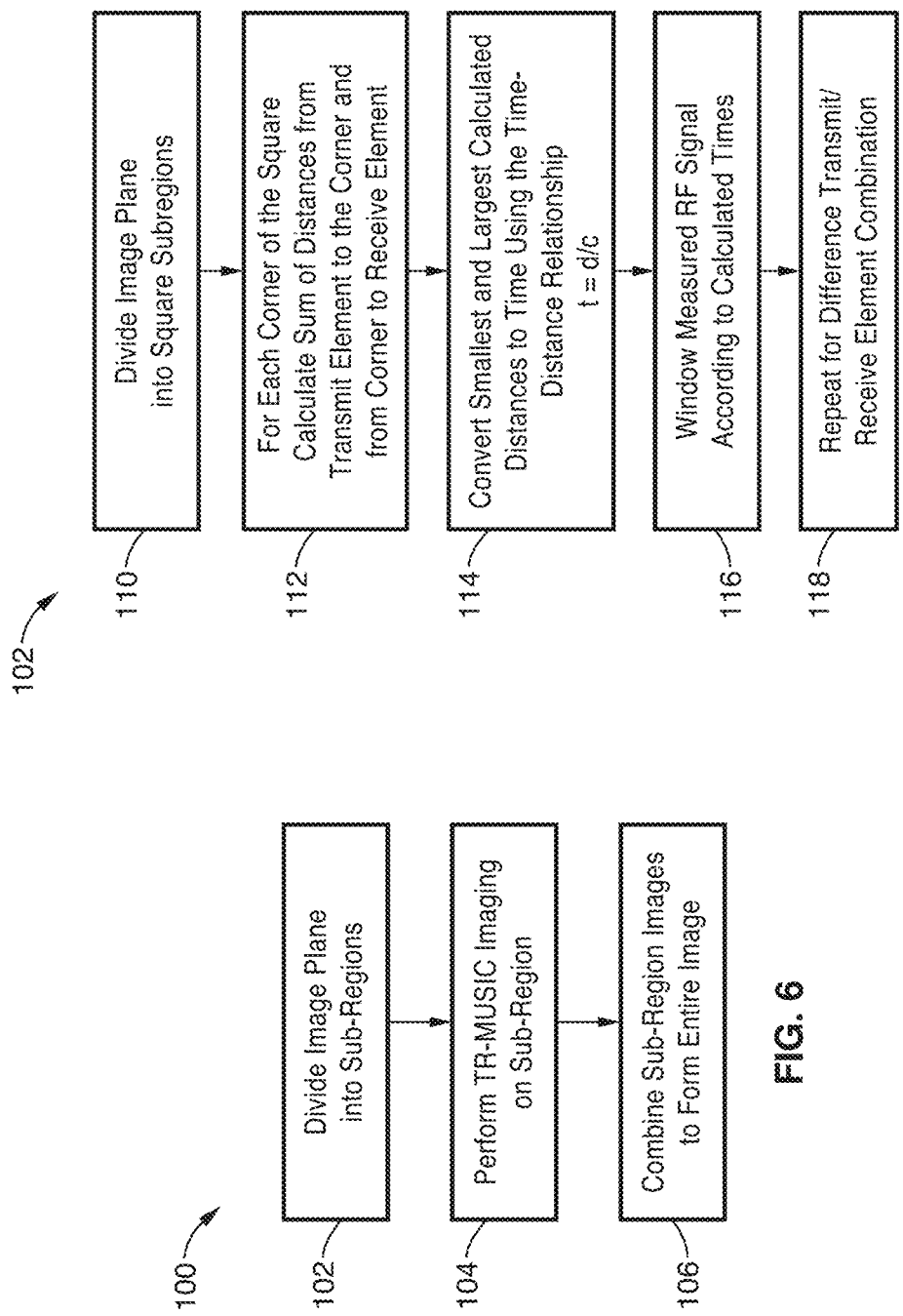
FIG. 6 shows a flow diagram of a windowed TR-MUSIC method of the present invention.
FIG. 7 is a flow diagram for dividing the image plane in accordance with the windowed method shown in FIG. 6.
Figure 8B:
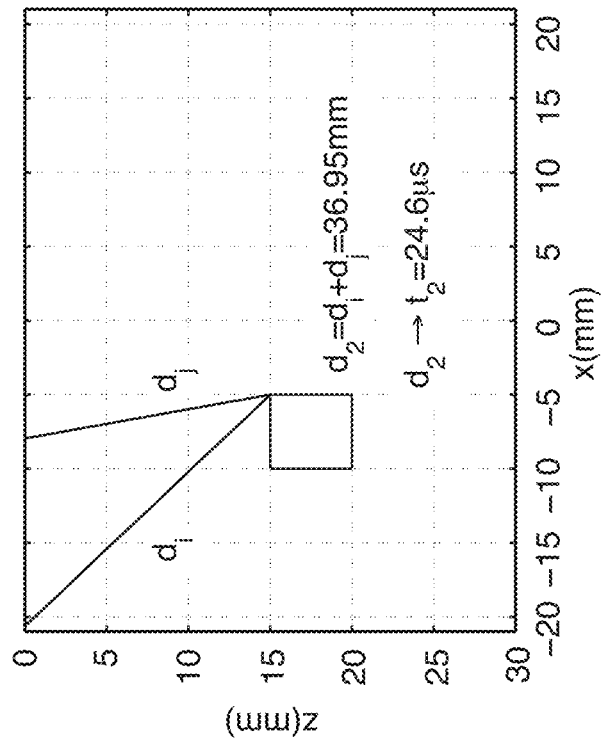
FIG. 8A through FIG. 8D show the distances from a transmitting element and a receiving element to the four corners of a chosen sub-region.
Figure 8A:
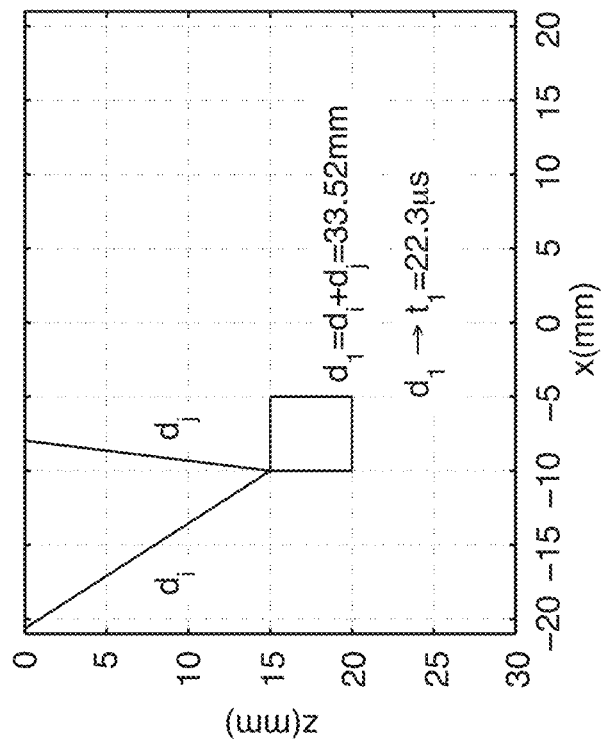
Figure 8D:
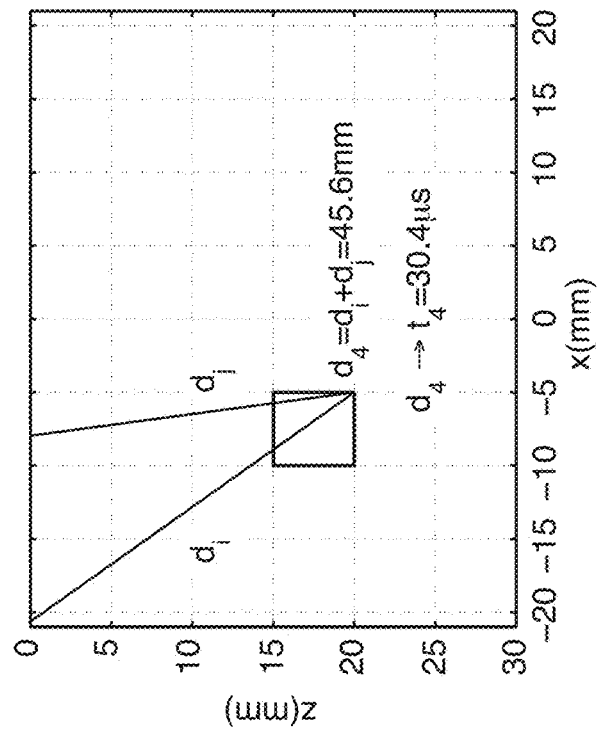
Figure 8C:
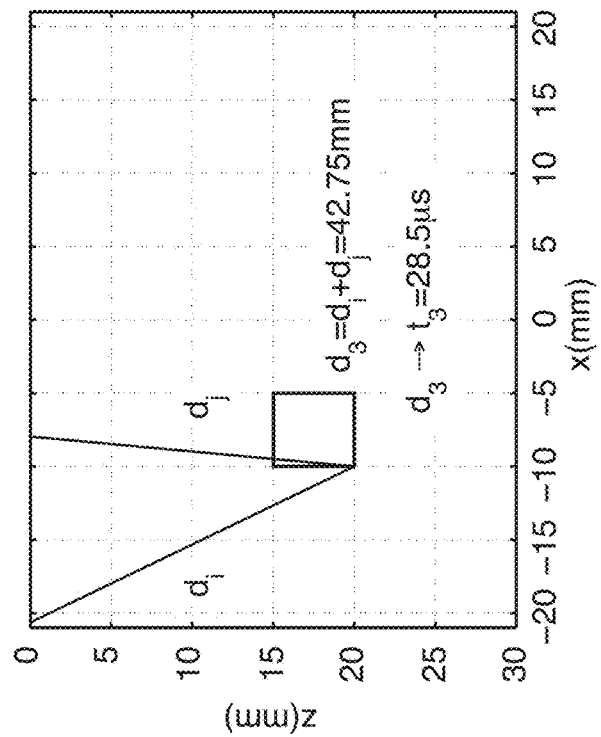

FIG. 6 shows a flow diagram of a windowed TR-MUSIC method 100 of the present invention. The imaging plane is divided into multiple sub-regions at step 102 and then each sub-region is imaged separately at step 104. The size of the sub-region in step 102 is chosen such that the number of scatterers within the sub-region is smaller than the number of transducer elements. All the recorded radio-frequency (RF) time signals are windowed such that the time samples of the window correspond to spatial locations of the chosen sub-region.

FIG. 7 is a flow diagram for dividing the image plane at step 102 in accordance with the windowed method shown in FIG. 6. FIGS. 8A through 8D illustrate graphically how windowing is performed for a square sub-region as detailed in step 102 of FIG. 7. The image plane is first divided into square sub-regions at step 110. For each corner of the sub-region, the sum of the distance from the corner to the transmitting element and the distance from the corner to the receiving element is computed at step 112, as shown in FIGS. 8A through 8D. At step 114, the times corresponding to the computed distances are calculated. The start and end times of the window are assigned as the times corresponding to the shortest and longest calculated distances (minimum and maximum). The shortest and longest calculated distances are converted to time using the time-distance relationship t=d/c. At step 116, the calculated time window is applied to the measured RF signal, and the time samples outside the window are set to zero. Finally, the process is repeated at step 118 different transmit-receive element combinations.

FIG. 8E shows an example of a measured received signal. FIG. 8F shows the resulting signal after setting the time samples outside the time window to zero.

Referring to step 104 of FIG. 6, to obtain an image of the chosen sub-region, the spectra are first calculated by performing Fast Fourier Transform (FFT) on the windowed signals. The TR matrix is then constructed (e.g. step 80 in FIG. 4) at a given frequency and eigenvalue decomposition (EVD) is performed. The image of the chosen sub-region is formed by calculating the pseudo-spectrum given by Eq. 36 (e.g. step 80 in FIG. 4). The images of all the sub-regions are then combined to form the entire image at step 106.

The advantage of this technique is that it allows the computations for forming the different images to be carried out in parallel. Since the emitted ultrasound waves from the transducer elements are unfocused, each windowed signal contains ultrasound waves that originate from an area between two ellipses whose foci are the locations of the transmitting element and the receiving element. Signals that originate from outside the chosen sub-region act as nuisance to the desired signals. However, since N×N time signals are needed to generate the TR matrix, the effects of the undesired signals is minimal due to the effective focusing on the selected sub-region.

Numerical Simulations and Phantom Experiments

Numerical simulations and phantom experiments were used to test the performance of our generalized and windowed TR-MUSIC algorithms. In the following, the simulation parameters and the phantom experiments are described. A calibration method is also presented to compensate for variations in element-to-element sensitivity and time response.

In the following discussion, a method for simulating an ultrasound linear transducer array is detailed. Each element of the array is excited sequentially and backscattered signals are recorded by all elements of the array. The backscattered signals originate from a number of point scatterers distributed in a homogeneous and attenuative medium, with an attenuation coefficient that varies linearly with frequency. In the simulations, the specifications of the transducer array 14 are chosen to be the same as those of a linear transducer array (Prosonic, HL5-10/40EPN) that we use with the investigational system for real-time synthetic-aperture ultrasound imaging (InnerVision, DAS2009). The array 14 has 128 elements 16 with a 325 μm pitch. The azimuthal length of each element is 300 μm, and the elevation length is 6 mm. The center frequency of each element is approximately 7.5 MHz and the 6-dB fractional bandwidth is approximately 65%.

In the simulations, all scatterers are positioned in the imaging plane. It is assumed that the scatterers have different compressibility from the background medium and the same density as the background medium. Since ultrasound scattering from compressibility fluctuations is not angular dependent, the Foldy-Lax model is used to calculate ultrasound scattered signals. This model accounts for multiple scattering. It has been shown that when scattering has no angular dependency, the TR-MUSIC algorithm is valid even when multiple scattering is non-negligible.

To simulate the spectrum of the signal received by element j after transmission from element i, Eq. 15 is combined with the Foldey-Lax model, i.e.

$$p_{i,j}(\omega) = \frac{2ik^4}{\omega\kappa_0} W_{ti}(\omega) W_{rj}(\omega) E(\omega) \sum_{m=1}^{M} \gamma_\kappa(r_m) \psi_i(r_m, \omega) \int\int_{S_j} g_0(r \mid r_m, \omega) ds.$$ Eq. 37

The function $\psi_i(r_m,\omega)$, accounts for multiple scattering among scatterers and can be solved using the Foldy-Lax set of linear equations that are given in matrix form by $$H\Psi_i = \Psi_i^{(in)},$$ Eq. 38 where $$\Psi_i = [\psi_i(r_1, \omega), \; \psi_i(r_2, \omega), \; \ldots, \; \psi_i(r_M, \omega)]^T,$$ Eq. 39 and $$\Psi_i^{(in)} = \left[ \int\int_{S_i} g_0(r_1 \mid r', \omega) ds', \right.$$ Eq. 40

$$\left. \int\int_{S_i} g_0(r_2 \mid r', \omega) ds', \ldots, \int\int_{S_i} g_0(r_M \mid r', \omega) ds' \right]^T,$$

are M-dimensional column vectors. H is a M×M matrix whose diagonal elements are unity, and off-diagonal elements are given by the product of the scatterers fluctuations in compressibility with the background Green's function evaluated at the locations of the scatterers; in particular, $$H_{m,n} = \delta_{m,n} - (1-\delta_{m,n})\gamma_\kappa(r_m)g_0(r_m|r_{m'}).$$ Eq. 41

Since the attenuation varies linearly with frequency, the complex wave number from Eq. 4 becomes:

$$k = \frac{2\pi f}{c_0} - i\alpha_0 f,$$ Eq. 42 where f denotes the frequency and $\alpha_0$ is the attenuation coefficient slope. Given the average sound speed of the medium and the complex wavenumber k, the double integrals of Eqs. 37 and 41 are numerically evaluated over the surfaces of the elements. The electromechanical transfer functions $W_t(\omega)$ and $W_r(\omega)$ are each approximated by the spectrum obtained by performing FFT on a Gaussian-modulated sinusoidal pulse with a center frequency of 7.5 MHz and a 6 dB fractional bandwidth. Time zero of the Gaussian-modulated sinusoidal pulse corresponds to the time where the leading pulse envelope falls below 60 dB. It is assumed that the excitation pulse is an impulse at time 0, and therefore, E(ω) is set to 1. The background compressibility $\kappa_0$ is arbitrarily set to one. The fluctuation in compressibility $\gamma_\kappa$ is set to 1 for all point scatterers. The time-dependent signals are calculated using the inverse FFT of the spectra obtained using Eq. 37.

To compensate for variations in element-to-element sensitivity and time response in the linear transducer array, the following calibration method was developed. The calibration uses a 50 μm diameter fishing line monofilament (Asso Fishing Line, SM3-08) placed perpendicular to the imaging plane. For each element, the transducer array 14 is translated horizontally such that the filament is located 2.5 cm axially from the center of the element 16. The element 16 transmits a pulse and receives the echo from the filament.

This pulse-echo experiment was repeated 10 times for each of the 128 elements and the radio frequency (RF) waveforms measured by each element are averaged to obtain the waveform $s_i(t)$, where i is the index for the transducer elements. A reference waveform $\bar{s}(t)$ was obtained by averaging all 128 waveforms (e.g. in accordance with step 93 of FIG. 5). Due to small variations in the position of the monofilament with respect to the center of the elements, a time-shift correction for each element 16 is obtained by cross correlation of the echo signal $s_i(t)$ with $\bar{s}(t)$ (e.g. in accordance with step 95 of FIG. 5).

The reference waveform is used with the time-aligned echo signal $s_i(t)$ to compute the compensation filter $r_i(t)$ that matches the echo signal $s_i(t)$ with the reference waveform $\bar{s}(t)$. The relation for the calibration filter applied before and after transmission is:

$$\bar{S}(\omega) = R_i^2(\omega) S_i(\omega),$$ Eq. 43 where $\bar{S}(\omega)$ is the spectrum of the reference signal $\bar{s}(t)$ and $R_i(\omega)$ is the spectrum of the calibration filer $r_i(t)$. Solving for the calibration filter of each element yields:

$$R_i(\omega) = \sqrt{\frac{\bar{S}(\omega)}{S_i(\omega)}}.$$ Eq. 44

Using Eq. 18, the filters R(ω) are used to calibrate the measured spectra prior to forming the inter-element transfer matrix K (e.g. with step 70 of FIG. 4).

A synthetic-aperture ultrasound imaging system (e.g. system 10 shown in FIG. 1) was used to image and acquire RF data from a tissue mimicking phantom (ATS laboratories Inc., ATS551). 128×128 RF time signals corresponding to the different transmit-receive element combinations were obtained. The phantom has an average attenuation coefficient slope of 0.5 dB/cm-MHz and an average sound speed of 1450 m/s. The phantom contains a number of nylon monofilaments that are approximately 50 µm in diameter. The filaments are arranged in groups of two. In each group, the two filaments are separated either axially or laterally. The edge-to-edge spacing between two filaments is 3 mm, 2 mm, 1 mm, 0.5 mm, 0.25 mm.

Numerical simulations were used to test the axial and lateral resolution obtained with the generalized TR-MUSIC algorithm of the present invention and compare them to those obtained with the original TR-MUSIC algorithm. Then, the effect of noise in ultrasound signals on image resolution was evaluated. Finally, the windowed TR-MUSIC algorithm of the present invention was tested by interrogating a medium 44 that contains 1000 randomly distributed point scatterers 42 (see FIG. 2).

To study the lateral and axial resolution of the generalized TR-MUSIC imaging algorithm, several cases of ultrasound scattered signals from two point scatterers 42 embedded in a homogeneous medium 44 were simulated. The attenuation coefficient slope of the medium 44 is 0.5 dB/cm-MHz and the average sound speed is 1500 m/s. In each case, either the lateral or the axial separation distance was varied between the two scatterers 42. The midpoint between the two scatterers 42 is located 2.5 cm axially from the center of the transducer 16. The separations between the two scatterers are: 8λ, 6λ, 4λ, 2λ, λ, λ/2, λ/4, λ/6, λ/8, λ/10, and λ/30, where λ, is the ultrasound wavelength. For each case, eigenvalue decomposition was performed on the TR matrix at the 7.5 MHz center frequency. In all simulation cases, that the number of nonzero eigenvalues was found to be exactly two.

Figure 9B:
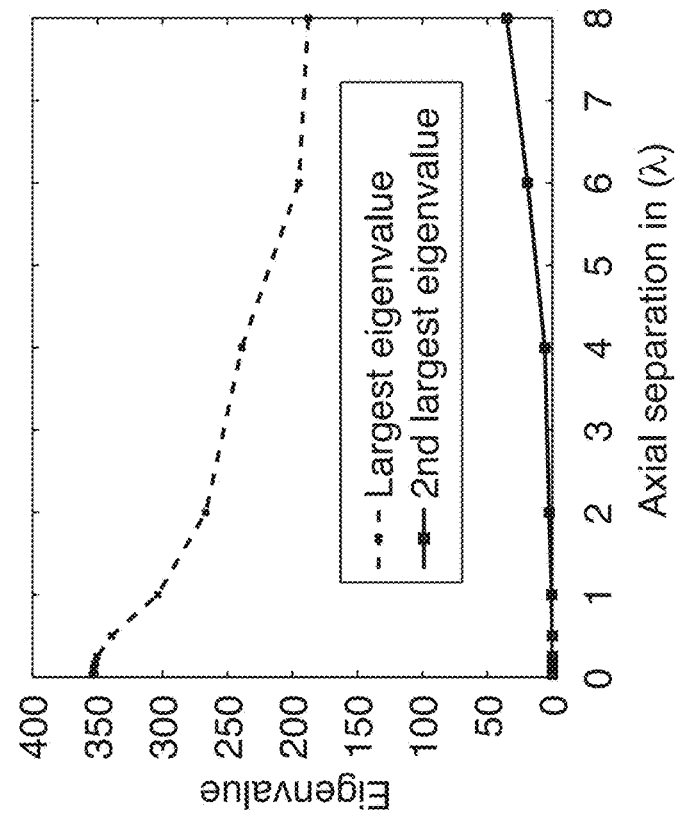
FIG. 9A through FIG. 9D show plots of the largest and second largest eigenvalues of the TR matrix versus the lateral separation FIG. 9A, and) the axial separation between the two scatterers FIG. 9B. Plots of FIG. 9C and FIG. 9D are magnified versions of the plots for the second largest eigenvalues in FIG. 9A and FIG. 9B, respectively.
Figure 9A:
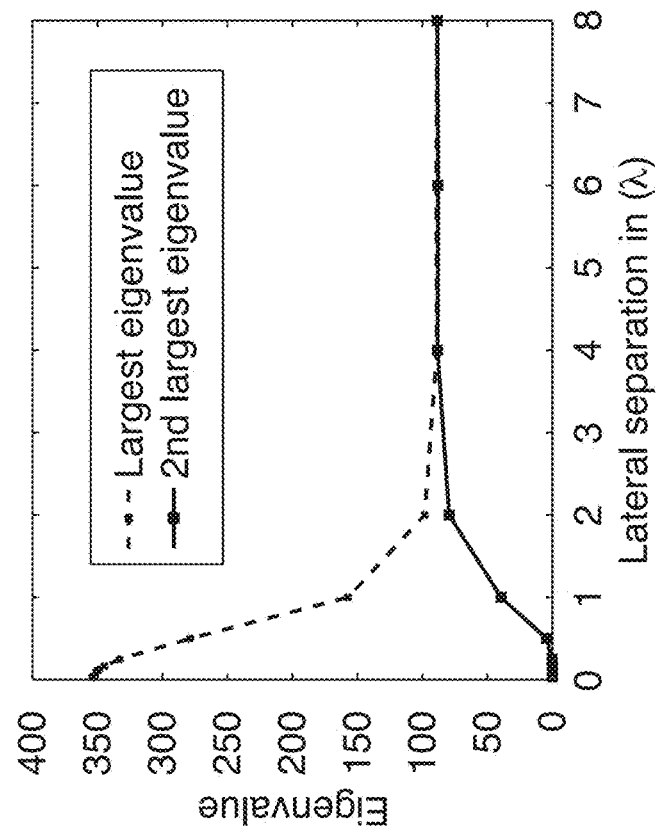
Figure 9D:
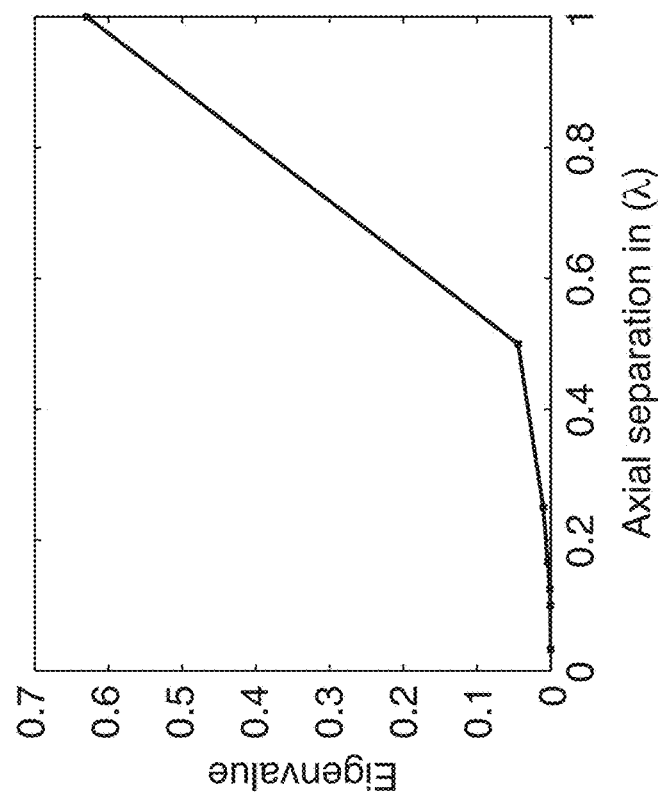
Figure 9C:
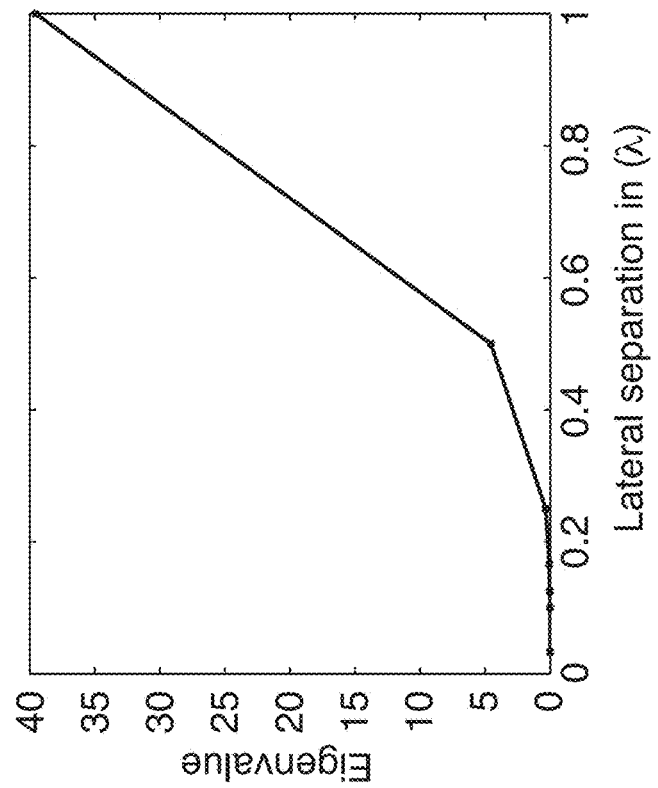

FIGS. 9A and 9B show plots of the largest and second largest eigenvalues of TR matrix, versus the lateral and axial separation distance, respectively. FIG. 9C and FIG. 9D show plots of the second largest eigenvalue of the TR matrix for lateral and axial separations between λ/30 and λ.

FIG. 9A and FIG. 9D indicate that, for both lateral and axial separations, the second largest eigenvalue decreases with decreasing scatterer separations and converges to zero, while the largest eigenvalue increases with decreasing scatterer separations and converges to a specific value. This result is expected, since the scatterers are less resolved as their separation decreases. For large lateral separations, the largest eigenvalue and the second largest eigenvalue are approximately equal. Furthermore, as the lateral separation approaches zero, the largest eigenvalue approaches four times its value when the separation is large. This result was shown by Prada in the case of two scatterers that are separated laterally and symmetric with respect the transducer array. Note that in FIG. 9B, the largest and the second-largest eigenvalues are not equal at large separations because the two scatterers are separately axially and therefore not symmetric with respect to the transducer array.

FIG. 9A and FIG. 9B also show that when the separation between the two scatterers 42 is small, the second largest eigenvalue is much smaller when the scatterers are separated axially compared to when they are separated laterally. This is a result of the CPSF of the transducer array 14. FIG. 10A through FIG. 10D show the CPFS for a point source located 25 mm axially from the center of the transducer array 14. The lateral profile at z=25 mm, and the axial profile at x=0 mm are also shown. The CPSF is obtained using Eq. 24. It clearly shows that the spatial extent of the CPSF is larger in the axial direction compared to that in the lateral direction.

When the pseudo-spectra given by Eq. 36 are calculated for the different cases of scatterer separations, we find that they peak at the exact scatterer locations. FIG. 11A through FIG. 11C shows lateral profiles of the pseudo-spectra for two scatterers separated laterally by λ/4, λ/10, and λ/30 respectively. Similarly, plots in FIG. 11D through FIG. 11F show profiles of the pseudo-spectra for two scatterers separated axially by λ/4, λ/10, and λ/30 respectively. These plot demonstrate that the TR-MUSIC imaging algorithm can achieve super-resolution. This is due to the fact that despite being much smaller than the largest eigenvalue, the second largest eigenvalue is never equal to zero.

The generalized TR-MUSIC algorithm of the present invention can achieve super-resolution. The attenuation and diffraction effects were compensated by using the exact expression for the vector $A_r$ to calculate the pseudo-spectrum of EQ. 36. The vector $A_r$ is given by:

$$A_r^T = \left[ \int\int_{S_1} \frac{\exp\left[-i\left(\frac{w}{c} - i\alpha\right)|r - r'|\right]}{4\pi|r - r'|} ds', \right.$$

$$\int\int_{S_2} \frac{\exp\left[-i\left(\frac{w}{c} - i\alpha\right)|r - r'|\right]}{4\pi|r - r'|} ds', \ldots ,$$

$$\left. \int\int_{S_N} \frac{\exp\left[-i\left(\frac{w}{c} - i\alpha\right)|r - r'|\right]}{4\pi|r - r'|} ds' \right],$$

Eq. 45

In the original TR-MUSIC algorithm, however, both attenuation and diffraction effects are ignored. To determine the effects of ignoring attenuation, we set the attenuation coefficient α to zero in the equation for the vector $A_r$. Similarly, the effects of ignoring diffraction effects of transducer elements were determined by removing the surface integrals in the equation for the vector $A_r$.

FIG. 12A through FIG. 12C show lateral profiles at z=25 mm for the pseudo-spectra of two point scatterers separated laterally by λ, λ/2, and λ/4, respectively. The pseudo-spectra in FIG. 12A through FIG. 12C are calculated by ignoring the effects of both attenuation and diffraction. FIG. 12D through FIG. 12F show the profiles corresponding to (a-c) when the attenuation is compensated. FIG. 12G through FIG. 12I shows the profiles corresponding to FIG. 12A through FIG. 12C when diffraction effects are compensated. FIG. 12J-12L shows the profiles corresponding to FIG. 12A through FIG. 12C when both attenuation and diffraction effects are compensated FIG. 13A through FIG. 13C show axial profiles at x=0 mm for the pseudo-spectra of two point scatterers separated axially by 4λ, 2λ, and λ, respectively. The pseudo-spectra in FIG. 13A through FIG. 13C are calculated by ignoring the effects of both attenuation and diffraction. FIG. 13D through FIG. 13F show the profiles corresponding to FIG. 13A-13C when the attenuation is compensated. FIG. 13G through FIG. 13I show the profiles corresponding to FIG. 13A through FIG. 13C when diffraction effects are compensated. FIG. 13J through FIG. 13L show the profiles corresponding to FIG. 13A through FIG. 13C when both attenuation and diffraction effects are compensated.

FIG. 12A through FIG. 12L and FIG. 13A through FIG. 13L show that, for a medium with an attenuation coefficient slope of 0.5 dB/cm-MHz, compensation for attenuation in the TR-MUSIC algorithm results in a minimal improvement in resolution. Compensation for diffraction effects of transducer elements, however, results in a significant improvement in both axial and lateral resolution. Note that when both attenuation and diffraction effects are ignored, the two scatterers separated laterally by $\lambda/4$ are resolved, while the scatterers separated axially by $2\lambda$ are not resolved. This result demonstrates that the lateral resolution is superior to the axial resolution. This behavior is a result of the spatial extent of the CPSF for a linear transducer array, as shown in FIG. 10A through FIG. 10D.

To determine the effects of additive noise on the resolution of the generalized TR-MUSIC algorithm, uncorrelated and zero mean Gaussian noise is added to the recorded time signals for each simulation case. The signal-to-noise ratio (SNR) is 25 dB. The SNR is defined according to the equation:

$$SNR = 20\log_{10}\left(\frac{S^2}{2\sigma^2}\right), \qquad \text{Eq. 46}$$

where $\sigma^2$ is the variance of the Gaussian noise, and S is the maximum amplitude of the weakest recorded signal. For each simulation case, the spectra of the noisy signals are calculated and the TR matrix is formed at frequency 7.5 MHz. We then calculate the pseudo-spectrum given by Eq. 36, where the exact expression for the vector $A_r$ is used.

FIG. 14A through FIG. 14C show lateral profiles of the pseudo-spectra for two scatterers separated laterally by $\lambda$, $\lambda/2$, and $\lambda/4$, respectively. Similarly, plots of FIG. 14D and FIG. 14E show profiles of the pseudo-spectra for two scatterers separated axially by $4\lambda$, $2\lambda$, and $\lambda$, respectively. It is clear that the two scatterers separated laterally by $\lambda/4$ and the two scatterers separated axially $\lambda$ are not resolved. These results demonstrate that noise degrades the resolution of the images obtained with the generalized TR-MUSIC algorithm of the present invention. The axial resolution is degraded more than the lateral resolution due the spatial extent of the CPSF.

To evaluate the performance of the original TR-MUSIC imaging algorithm when the number of scatterers exceeds the number of transducer elements, Eq. 37 was used to simulate scattering from 1000 point scatterers 42 randomly distributed in the imaging plane of a homogeneous medium 44. The attenuation coefficient slope of the medium is 0.5 dB/cm-MHz and the average sound speed is 1500 meter/second. The lateral extent of the scatters is 4.2 cm, which corresponds to the length of the array, and the axial extent is 3 cm, as shown in FIG. 15A.

FIG. 15C shows the eigenvalues of the TR matrix calculated at the 7.5 MHz center frequency. The TR matrix has no zero eigenvalues, and therefore, it has full rank N. FIG. 15B shows the image obtained by calculating the pseudo-spectrum of Eq. 36 with the 20 eigenvectors that have the lowest eigenvalues. Both attenuation and diffraction effects are compensated during the computation of the pseudo-spectrum. The resulting image is very noisy and contains bright spots that do not correspond to the scatterer locations. Similar results are obtained when the pseudo-spectrum is calculated using a different number of eigenvectors. These results suggest that the original TR-MUSIC algorithm is not valid when the number of scatterers exceeds the number of transducer elements.

The windowed TR-MUSIC algorithm of the present invention was applied to the same simulated ultrasound scattered signals. A 5 mm×5 mm square region was chosen, and the windowed TR-Music method 100 shown in FIG. 6 was used to generate the image of the sub-region.

FIG. 16A shows the location of the scatterers within a given sub-region. FIG. 16B shows the eigenvalues of the TR matrix corresponding to the chosen sub-region. The number of nonzero eigenvalues is greater than the number of point scatterers within the sub-region. This happens because the windowed time signals contain contributions from outside the selected sub-region. FIGS. 16A and 16B show the images obtained using T-R imaging step 104 (the eigenvectors with the 20 and 100 lowest eigenvalues, respectively). The two images are very noisy and the point scatterers are not accurately located. Imaging using a different number of eigenvectors yields similar results.

Next, a 1 mm×1 mm square region was selected and the windowed TR-MUSIC algorithm was used to generate the corresponding image. FIG. 17A shows the location of the scatterers within the chosen sub-region. FIG. 17B shows the eigenvalues of the TR matrix corresponding to the chosen sub-region. It is clear that the number of nonzero eigenvalues is greater than the number of point scatterers within the sub-region. FIG. 17C and FIG. 17D show the images obtained using the eigenvectors with the 20 and the 100 lowest eigenvalues, respectively. The two point scatterers within the chosen sub-region are resolved in both images. This result suggests that when the number of scatterers is large, the sub-region must be small enough to minimize the effects of the nuisance signals that originate from outside the chosen sub-region. Note that image resolution is higher when using 20 eigenvectors compared to 100 eigenvectors to calculate the pseudo-spectrum. This is expected, since the TR-MUSIC algorithm requires using eigenvectors with zero eigenvalues to calculate the pseudo-spectrum.

The images of FIG. 17C and FIG. 17D show some low-intensity artifacts that don't correspond to the point scatterers within the region. These artifacts are apparent because the lowest eigenvalues used to calculate the pseudo-spectrum are not exactly equal to zero. Images similar to FIG. 17C are obtained when eigenvectors between 5 and 20 are used to calculate the pseudo-spectrum. However, the images degrade when fewer than 5 eigenvectors or more than 30 eigenvectors are used to calculate the pseudo-spectrum. Further modification may be used to optimize the sub-region size and the number of eigenvectors used to calculate the pseudo-spectrum.

The entire image of the interrogated plane is formed by combining the images of the 1 mm×1 mm sub-regions, as provided in step 106 of method 100. FIG. 18A shows the scatterer distribution, and FIG. 18B shows the resulting image. FIGS. 18C and 18E show the scatterer distribution in a region close to the transducer array, and a sub-region far from the transducer array, respectively. FIGS. 18D and 18F show the corresponding images. The resolution of the region closer to the array is much higher than the resolution of the region farther away from the transducer array. Furthermore, the images of point scatterers that are far off axis have a slanted orientation. The lateral resolution is also better than the axial resolution. These results are caused by the spatial extent of the CPSF of the transducer array. These numerical examples clearly demonstrate that the windowed TR-MUSIC imaging method 100 of the present invention can accurately locate the point scatterers when their number is larger than the number of the transducer elements.

Next, the windowed TR-MUSIC method 100 of the present invention was tested against the original TR-MUSIC algorithm on phantom data acquired with a synthetic-aperture (SA) ultrasound imaging system. The quality and the resolution of the images obtained with TR-MUSIC algorithms to those obtained with the SA system was compared. The images obtained with the SA system are formed using synthetic-aperture ultrasound imaging techniques.

FIG. 19A shows a B-mode image of the ATS phantom obtained with the SA ultrasound system. The spectra of the measured RF signals are used to calculate the TR matrix at the 7.5~MHz frequency. The eigenvalues of the TR matrix are shown in FIG. 19C. FIG. 19B is the image obtained using the TR-MUSIC algorithm without applying the windowing technique. The image is obtained by calculating the pseudo-spectrum of Eq. 36 with the 20 eigenvectors that have the lowest eigenvalues (FIG. 19C). Both attenuation and diffraction effects are accounted for during the computation of the pseudo-spectrum. The image is very noisy and many of the filaments are not resolved. Similar results were obtained when calculating the pseudo-spectrum using a different number of eigenvectors. Although the number monofilaments is fewer than the number of transducer elements, the original TR-MUSIC algorithm cannot resolve all the filaments due the full rank of the TR matrix. The full rank is the result of ultrasound scattering from inhomogeneities within the phantom which create the observed speckle in the SA ultrasound image.

FIG. 20A shows a B-mode image of the ATS phantom obtained using the SA ultrasound system. FIG. 20B shows the entire image that is formed by combining the images of 5 mm×5 mm sub-regions obtained using the windowed TR-MUSIC method 100 of the present invention. In each sub-region, the pseudo-spectrum is calculated using the TR-matrix eigenvectors with the 20 lowest eigenvalues. FIG. 20C and FIG. 20D show magnified images of the filaments that are separated laterally by 1 mm, 0.5 mm, and 0.25 mm corresponding to FIG. 20A and FIG. 20B, respectively. FIG. 14E and FIG. 14F show magnified images of the filaments that are separated axially by 1 mm, 0.5 mm, and 0.25 mm corresponding to FIG. 20A and FIG. 20B, respectively. All the filaments are well resolved. The lateral resolution of the image obtained using the windowed TR-MUSIC method 100 of the present invention is far superior to the lateral resolution of the image obtained using the InnerVision system. Note that, as a result of the CPSF, the resolution of the windowed TR-MUSIC algorithm is higher for the filaments closer to transducer array compared to the filaments farther away from the array.

Next, the methods of the present invention were tested on phantoms simulating extended targets. Four tissue-mimicking, phantoms (TMPs) with embedded glass spheres were constructed. Phantom 1 contains five well-separated glass spheres with a diameter of 2.9 mm, 1.8 mm, 1.5 mm, 1 mm, and 0.55 mm. The phantom 1 was used to test the effect of target size (or ka value where k is the wavenumber and a is the effective radius of scatterers) on the number of non-zero eigenvalues of the TR matrix, and to test the capability of the TR-MUSIC algorithm to provide the shape information. Approximately 100 glass spheres were randomly distributed in planes inside phantoms 2, 3, and 4. The spheres have a diameter ranging from 0.25 mm to 0.3 mm, 0.5 mm to 0.6 mm, and 0.8 to 1.2 mm, for phantoms 2, 3, and 4, respectively. These phantoms are used to evaluate the capability of the TR-MUSIC algorithm to image numerous extended targets, and to test the effect of the target size on image characteristics.

The phantoms are scanned using an SA imaging system (InnerVsion DAS2009) with a 128-element transducer array (Prosonic, HL5-10/40EPN). The ultrasound system provides access to all the RF measured signals (128×128 RF signals), and generates a B-mode image using a SA imaging technique. The TMPs are also radiographed using X-ray mammography.

The SA imaging system was used to scan each sphere of phantom 1 separately. The 128×128 TR-matrix is calculated at the frequency of 3.65 MHz. FIG. 21 shows the spectrum of the first eight eigenvalues as a function of ka. It is clear that the number of dominant eigenvalues increases with increasing ka. For a given ka, the non-dominant (noise) eigenvalues converge towards a small value (relative to the largest eigenvalue).

Images of the glass spheres are formed using the pseudo-spectrum given by Eq. 36. The plots of FIG. 21 were used to estimate the number of noise eigenvectors to use in the pseudo-spectrum. FIG. 22A through FIG. 22D show the TR-MUSIC images of four glass spheres with a diameter of 2.9 mm, 1.5 mm, 1 mm, and 0.55 mm, respectively, where the number of noise eigenvectors used to calculate the pseudo-spectra are 123, 124, 125, and 126, respectively. The TR-MUSIC images provide no shape information. The lateral extensions of the bright regions of the images are not representative of the sphere sizes. Approximate sizes of the spheres may be deduced from the axial extensions of the bright regions. These regions, however, appear somewhat elongated. FIG. 23A through FIG. 23D, FIG. 24A through FIG. 24D, and FIG. 25A through FIG. 25D show comparisons of images obtained using different imaging modalities of phantoms 2, 3, and 4, respectively.

Figure 23A:
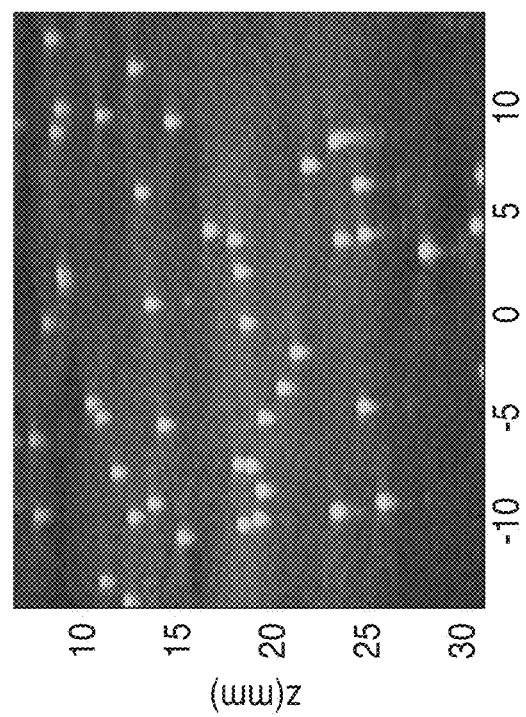

FIG. 23A, FIG. 24A and FIG. 25A show the X-ray mammography images, which are inverted for better comparison with the ultrasound images.

Figure 23B:
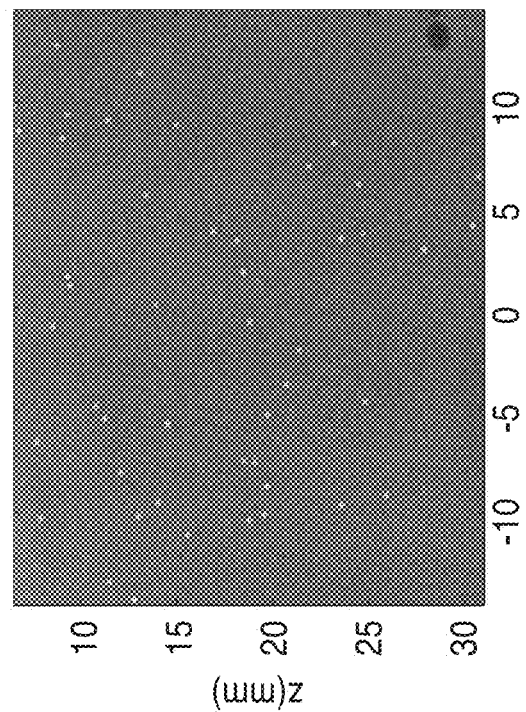

The corresponding SA images are shown in FIG. 23B, FIG. 24B and FIG. 25B. It is clear that the SA images have lower resolution compared to the X-ray mammography images. In the SA image of phantom 2 shown in FIG. 23B, the glass spheres appear larger than their actual sizes, and some closely-separated spheres appear as one. In the SA image of phantom 3 shown in FIG. 24B, a single sphere appears as multiple bands with decreasing intensity in the axial direction. This artifact is more prominent in the SA image of phantom 4 shown in FIG. 25B, where the glass spheres are larger than those in phantoms 2 and 3. The bands are caused by multiple reflections of ultrasound waves inside the spheres.

Figure 23D:
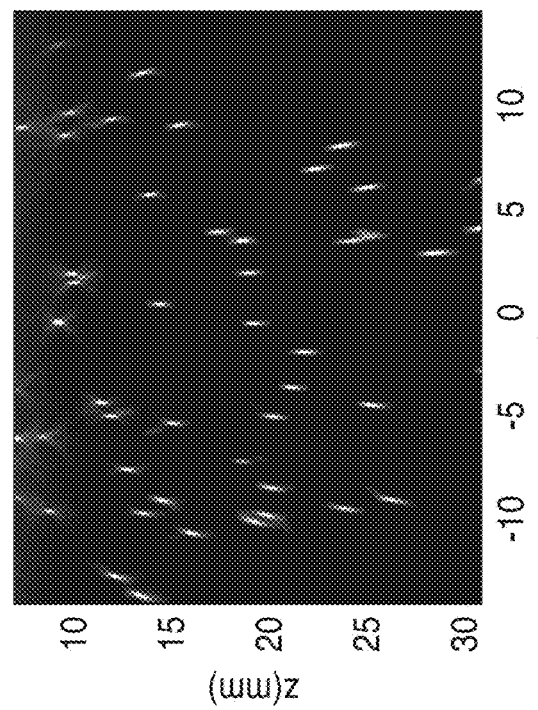
Figure 23C:
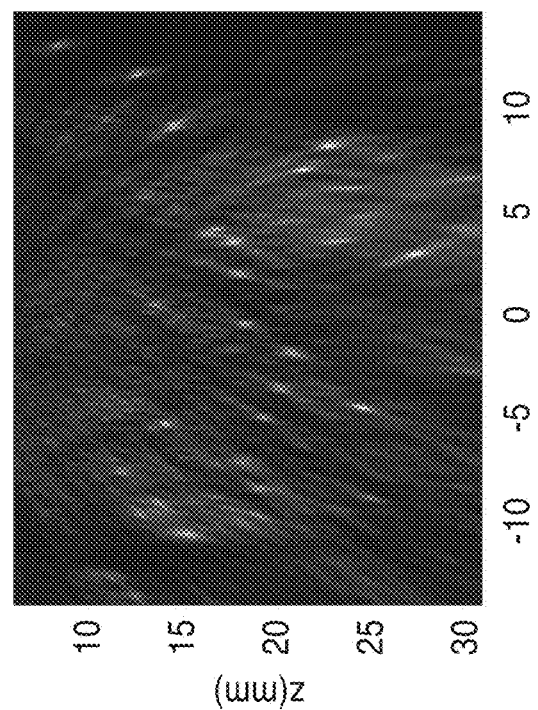
Figure 25D:
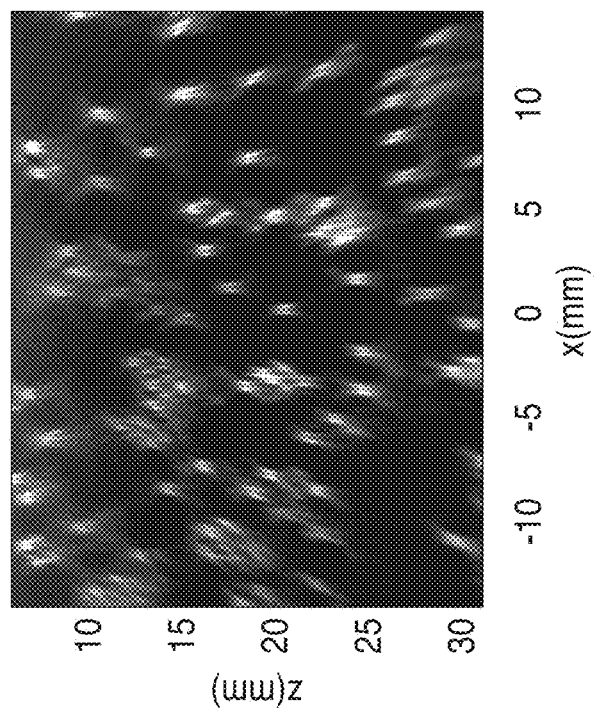
Figure 25C:
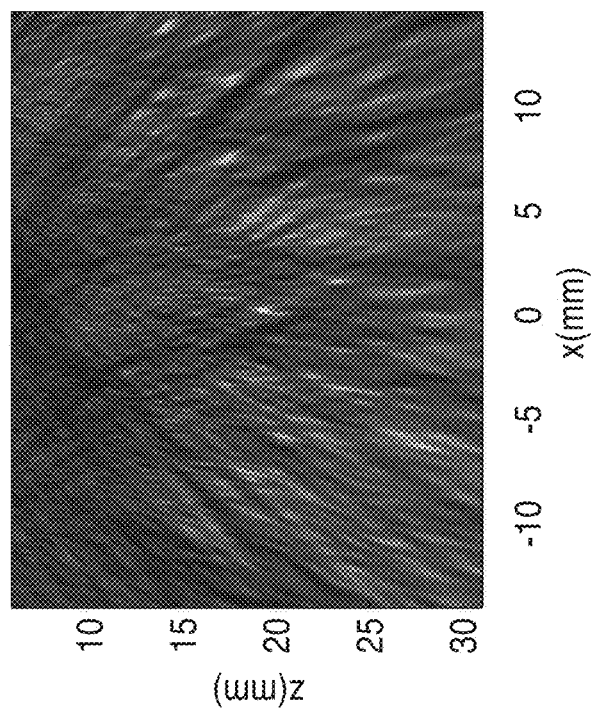

The TR-MUSIC images of phantoms 2, 3, and 4, obtained using 20 noise eigenvectors at 3:65 MHz are shown in FIG. 23C, FIG. 24C and FIG. 25C. The TR-MUSIC image of phantom 2 shown in FIG. 23C is noisy and many of the spheres are not imaged. Similar characteristics are observed in the TR-MUSIC image of phantom 3 shown in FIG. 24C. The image of phantom 4 shown in FIG. 25C is dominated by noise and almost none of the spheres are resolved. The degradation of image quality with increasing sphere size is caused by the increase in the rank of the TR matrix with increasing sphere size.

To improve the quality of the TR-MUSIC images, the windowing technique 100 of the present invention was employed, where TR-MUSIC images of 5 mm×5 mm square sub-regions were combined. The sub-regions are overlapped by 50%, and the TR matrices are calculated at 3.65 MHz. To simplify the calculation of the pseudo-spectra, the number of noise eigenvectors were we conservatively fixed to 64.

The resulting TR-MUSIC images obtained with the windowing method 100 are shown in FIG. 23D, FIG. 24D and FIG. 25D. These images demonstrate that the windowing method 100 of the present invention significantly reduces image noise. All the spheres of phantoms 2 and 3 are clearly observed, while the closely-separated spheres of phantom 4 are difficult to resolve. The images provide no shape information. Compared to the SA images, the TR-MUSIC images have a higher lateral resolution. The elongation artifact observed previously in the images of phantom 1 is also apparent in the TR-MUSIC images of phantoms 2, 3, and 4. This artifact reduces the axial resolution.

CONCLUSIONS

A generalized TR-MUSIC algorithm was developed to account for the attenuation in the medium and the finite-size effects of the transducer elements. It was demonstrated that that the generalized algorithm yields higher resolution images compared to those obtained without accounting for attenuation or diffraction effects. Without noise in the recorded RF signals, the algorithm yields super-resolution. When noise corrupts the recorded signals, the image resolution decreases. The axial resolution degrades more than the lateral resolution because of the spatial extent of the coherent point spread function. A windowed TR-MUSIC algorithm was also developed for imaging point scatterers when their number exceeds the number of transducer elements. This method is based on dividing the imaging plane into sub-regions and applying the TR-MUSIC algorithm to the windowed backscattered signals corresponding to each sub-region. The images of all sub-regions are then combined to form the total image.

It was shown that to optimize results, the sub-region size and the number of eigenvectors used to calculate the pseudo-spectrum can be chosen accordingly. The sub-region size is preferably small enough such that that the number of scatterers within is much smaller than the number of transducer elements, so that the effects of the nuisance signals from outside the sub-region are negligible. The number of eigenvectors is preferably chosen such that the corresponding eigenvalues are close to zero. It was demonstrated through a phantom experiment that the windowed TR-MUSIC algorithm yields a significantly higher image quality compared to the original TR-MUSIC algorithm. It was also shown that the lateral resolution obtained using the windowed TR-MUSIC algorithm is far superior to the lateral resolution of the image obtained using synthetic-aperture imaging.

The windowed TR-MUSIC algorithm of the present invention is ideally suited for detection of breast microcalcifications.

Embodiments of the present invention may be described with reference to flowchart illustrations of methods and systems according to embodiments of the invention, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

From the discussion above it will be appreciated that the invention can be embodied in various ways, including the following:

1. A method of performing ultrasound imaging of a medium, comprising: exciting a first transducer element in an array of transducer elements to direct an ultrasound signal into a target region of the medium; receiving a backscatter signal from the target region within the medium with the array of transducer elements; generating an inter-element transfer matrix of the received backscatter signal; generating a generalized time-reversal (TR) matrix from the inter-element transfer matrix; and generating a pseudo-spectrum for generalized TR-Music imaging of the target region.

2. A method as recited in any of the preceding embodiments, wherein generating an inter-element transfer matrix comprises calculating the inter-element transfer matrix as a function of an electro-mechanical response of each transducer element in the array.

3. A method as recited in any of the preceding embodiments, wherein generating an inter-element transfer matrix comprises calculating the inter-element transfer matrix as a function of a diffraction response of each transducer element in the array.

4. A method as recited in any of the preceding embodiments, wherein generating an inter-element transfer matrix comprises calculating the inter-element transfer matrix as a function of attenuation in the target region.

5. A method as recited in any of the preceding embodiments, wherein the diffraction response of each transducer element is a function of the finite size effects of the array of transducer elements.

6. A method as recited in any of the preceding embodiments, wherein the inter-element transfer matrix K is calculated according to the function:

$$K = \frac{2ik^4}{\omega \kappa_0} F(\omega) \int \int\int_{V_0} \gamma_\kappa(r_0) A_{r_0} A_{r_0}^T dv_0;$$

wherein the superscript T denotes the transpose and $A_{r_0}$ is an N-dimensional column vector given by:

$$[a_1(r_0,\omega) a_2(r_0,\omega) \ldots a_N(r_0,\omega)].$$

7. A method as recited in any of the preceding embodiments, wherein the generalized time-reversal matrix is calculated according to:

$$T = \frac{-4k^8}{(\omega \kappa_0)^2} |F(\omega)|^2 \sum_{m=1}^{M} \sum_{m'=1}^{M} \Lambda_{m,m'} A_{r_m}^* A_{r'_m}^T;$$

wherein $$A_{r_m}^T = [\,a_1(r_m, \omega) \quad a_2(r_m, \omega) \quad \ldots \quad a_N(r_m, \omega)\,];$$

and $$\Lambda_{m,m'} = \gamma_\kappa(r_m)\gamma_\kappa(r'_m)\langle A_{r_m}, A_{r'_m}\rangle.$$

8. A method as recited in any of the preceding embodiments, wherein the inter-element transfer matrix is calculated as according to the function $g_0(\omega,r|r_0)$, wherein:

$$g_0(\omega, r \mid r_0) = \frac{\exp - i\underline{k}|r - r_0|}{4\pi|r - r_0|};$$

$$\underline{k} = \frac{\omega}{c} - i\alpha;$$

and wherein $k=\omega/c$ is the real wave number, $\omega$ is the angular frequency, $\alpha$ is the amplitude attenuation coefficient, c is the average sound speed, and i is the imaginary unit.

9. A method as recited in any of the preceding embodiments, wherein the inter-element transfer matrix is calculated as according to the function $a_i(r_0,\omega)$ over a surface of a transducer element is $$a_i(r_0, \omega) = \int\int_{S_i} g_0(r \mid r_0) ds;$$

and wherein r corresponds to a location of a wavefield resulting from a point source at a location $r_0$.

10. A method as recited in any of the preceding embodiments, wherein the pseudo-spectrum is calculated according to the equation:

$$PS(r) = \frac{1}{\sum_{m_0=M+1}^{N} |\langle \mu_{m_0}^*, A_r\rangle|^2};$$

wherein M corresponds to a number of scatterers in the target region, N corresponds to the number transducer elements in the array, $\mu_{m_0}$ corresponds to an eigenvector with a zero eigenvalue, $\lambda_m$ corresponds to an eigenvector with a positive eigenvalue, and $A^*_{r_m}$ corresponds to vectors associated with the scatterers.

11. A method as recited in any of the preceding embodiments, wherein variations in sensitivity and time response characteristics from the individual transducer elements in the array are compensated by calibrating the array.

12. A method as recited in any of the preceding embodiments, wherein calibrating the array comprises: sequentially transmitting a pulse toward a target and receiving an echo signal from said target for each element in the array; obtaining an RF waveform of the echo signal for all transducer elements in the array; obtaining a reference waveform by averaging the RF waveforms for each element; calculating a time-shift correction for each element in the array; applying the calculated time shift correction to the RF waveform; and generating a calibration filter from corrected RF waveform.

13. A method as recited in any of the preceding embodiments, wherein receiving a backscatter signal further comprises: dividing an imaging plane of the target region into a plurality of sub-regions; imaging each sub-region in the plurality of sub-regions separately; and combining each sub-region to form an entire image of the target region.

14. A method as recited in any of the preceding embodiments, wherein the size of the sub-region is chosen such that the number of scatterers within the sub-region is smaller than the number of transducer elements in the array.

15. A method as recited in any of the preceding embodiments, wherein spatial locations in each sub-region correspond with windowed time samples within the imaging plane.

16. A method as recited any of the preceding embodiments, wherein the medium comprises a tissue region within the body of a patient.

17. A method of performing ultrasound imaging of a target region of a medium, comprising: exciting a first transducer element in an array of transducer elements to direct an ultrasound signal into the target region; receiving a backscatter signal from the target region with the array of transducer elements; and performing time-reversal imaging by: dividing an imaging plane into multiple sub-regions; imaging each sub-region separately; and combining each sub-region to form an entire image.

18. A method as recited in any of the preceding embodiments, wherein the target region comprises a plurality of point scatterers, and wherein the method is configured to image the target region when the number of point scatterers in the target region of tissue exceeds the number of transducer elements in the array.

19. A method as recited in any of the preceding embodiments, wherein the target region comprises one or more extended targets comprising an extended region beyond a the dimensions of a point scatterer.

20. A method as recited in any of the preceding embodiments, wherein each sub-region is shaped to overlap with adjacent sub-regions and sized such that the number of scatterers within each sub-region is smaller than the number of transducer elements in the array.

21. A method as recited in any of the preceding embodiments, wherein spatial locations in each sub-region correspond with windowed time samples within the imaging plane.

22. A method as recited in any of the preceding embodiments: wherein each sub-region comprises a square region having four corners; wherein dividing the image into sub-regions comprises: calculating the sum of the distances from each corner to the first transmitting element and a second receiving element in the array; assigning windowed time samples having start and end times corresponding to the calculated distances; and muting time samples outside said start and end times.

23. A method as recited in any of the preceding embodiments, wherein imaging each sub-region comprises: generating an inter-element transfer matrix of the received backscatter signal; generating a generalized time-reversal (TR) matrix from the inter-element transfer matrix of the sub-region; and generating a pseudo-spectrum for each sub-region.

24. A method as recited in any of the preceding embodiments, wherein generating an inter-element transfer matrix comprises calculating the inter-element transfer matrix as a function of the electro-mechanical response of each transducer element in the array.

25. A method as recited in any of the preceding embodiments, wherein generating an inter-element transfer matrix comprises calculating the inter-element transfer matrix as a function of the diffraction impulse response of each transducer element in the array.

26. A method as recited in any of the preceding embodiments, wherein generating an inter-element transfer matrix comprises calculating the inter-element transfer matrix as a function of the attenuation in the target region.

27. A method as recited in any of the preceding embodiments, wherein the diffraction response of each transducer element is a function of the finite size effects of the array of transducer elements.

28. A method as recited in any of the preceding embodiments, wherein the medium comprises a tissue region within the body of a patient.

29. An ultrasound imaging system, comprising: (a) a processor; and (b) programming executable on said processor for: (i) exciting a first transducer element in an array of transducer elements to direct an ultrasound signal into a target region of tissue; (ii) receiving a backscatter signal from the target region with the array of transducer elements; and (iii) performing time reversal imaging by: generating an inter-element transfer matrix of the received backscatter signal; generating a generalized time-reversal (TR) matrix from the inter-element transfer matrix; and generating a pseudo-spectrum for generalized TR-Music imaging of the target region.

30. A system as recited in any of the preceding embodiments, wherein generating an inter-element transfer matrix comprises calculating the inter-element transfer matrix as a function of an electro-mechanical response of each transducer element in the array.

31. A system as recited in any of the preceding embodiments, wherein generating an inter-element transfer matrix comprises calculating the inter-element transfer matrix as a function of a diffraction impulse response of each transducer element in the array.

32. A system as recited in any of the preceding embodiments, wherein generating an inter-element transfer matrix comprises calculating the inter-element transfer matrix as a function of attenuation in the target region.

33. A system as recited in any of the preceding embodiments, wherein finite size effects of the array of transducer elements are factored in calculating the inter-element response matrix.

34. A system as recited in any of the preceding embodiments, wherein the inter-element transfer matrix K is calculated according to the equation:

$$K = \frac{2i\underline{k}^4}{\omega\kappa_0} F(\omega) \int\int\int_{V_0} \gamma_\kappa(r_0) A_{r_0} A_{r_0}^T dv_0;$$

wherein the superscript T denotes the transpose and $A_{r_0}$ is an N-dimensional column vector given by:

$$[a_1(r_0,\omega) a_2(r_0,\omega) \ldots a_N(r_0,\omega)].$$

35. A system as recited in any of the preceding embodiments, wherein the generalized time-reversal matrix is calculated according to:

$$T = \frac{-4\underline{k}^8}{(\omega\kappa_0)^2}|F(\omega)|^2 \sum_{m=1}^{M}\sum_{m'=1}^{M} \Lambda_{m,m'} A_{r_m}^* A_{r_m'}^T;$$

wherein:

$$A_{r_m}^T = [\,a_1(r_m,\omega)\ \ a_2(r_m,\omega)\ \ \ldots\,,\ a_N(r_m,\omega)\,];$$

and $$\Lambda_{m,m'} = \gamma_k(r_m)\gamma_k(r_m')\langle A_{r_m}, A_{r_m'}\rangle.$$

36. A system as recited in any of the preceding embodiments, wherein the inter-element transfer matrix is calculated as according to the function $g_0(\omega),r|r_0)$, wherein:

$$g_0(\omega, r\,|\,r_0) = \frac{\exp-i\underline{k}|r-r_0|}{4\pi|r-r_0|};$$

$$\underline{k} = \frac{\omega}{c} - i\alpha;$$

and wherein $k=\omega/c$ is the real wave number, $\omega$ is the angular frequency, $\alpha$ is the amplitude attenuation coefficient, c is the average sound speed, and i is the imaginary unit.

37. A system as recited in any of the preceding embodiments, wherein the inter-element transfer matrix is calculated as according to the function $a_i(r_0,\omega)$ over a surface of a transducer element is $$a_i(r_0,\omega) = \int\int_{S_i} g_0(r\,|\,r_0)ds;$$

and wherein r corresponds to a location of a wavefield resulting from a point source at a location $r_0$.

38. A system as recited in any of the preceding embodiments, wherein the pseudo-spectrum is calculated according to the equation:

$$PS(r) = \frac{1}{\sum_{m_0=M+1}^{N} |\langle \mu_{m_0}^*, A_r\rangle|^2};$$

wherein M corresponds to a number of scatterers in the target region, N corresponds to the number transducer elements in the array, $\mu_{m_0}$ corresponds to an eigenvector with a zero eigenvalue, $\lambda_m$ corresponds to an eigenvector with a positive eigenvalue, and $A^*_{r_m}$ corresponds to vectors associated with the scatterers.

39. A system as recited in any of the preceding embodiments, wherein variations in sensitivity and time response characteristics from the individual transducer elements in the array are compensated by calibrating the array.

40. A system as recited in any of the preceding embodiments, wherein calibrating the array comprises: averaging an RF waveform obtained for all transducer elements in the array; and calculating a time-shift correction for each element in the array.

41. A system as recited in any of the preceding embodiments, wherein receiving a backscatter signal further comprises: dividing an imaging plane of the target region into a plurality of sub-regions; imaging each sub-region in the plurality of sub-regions separately; and combining each sub-region to form an entire image of the target region.

42. A system as recited in any of the preceding embodiments, wherein the size of the sub-region is chosen such that the number of scatterers within the sub-region is smaller than the number of transducer elements in the array.

43. A system as recited in any of the preceding embodiments, wherein spatial locations in each sub-region correspond with windowed time samples within the imaging plane.

44. An ultrasound imaging system, comprising: (a) a processor; and (b) programming executable on said processor for: (i) exciting a first transducer element in an array of transducer elements to direct an ultrasound signal into a target region of tissue; (ii) receiving a backscatter signal from the target region with the array of transducer elements; and (iii) performing time-reversal imaging by: dividing an imaging plane into multiple sub-regions; imaging each sub-region separately; and combining each sub-region to form an entire image.

45. A system as recited in any of the preceding embodiments, wherein the target region comprises a plurality of point scatterers, and wherein the method is configured to image the target region when the number of point scatterers in the target region of tissue exceeds the number of transducer elements in the array.

46. A system as recited in any of the preceding embodiments, wherein each sub-region is shaped to overlap with adjacent sub-regions and sized such that the number of scatterers within each sub-region is smaller than the number of transducer elements in the array.

47. A system as recited in any of the preceding embodiments, wherein spatial locations in each sub-region correspond with windowed time samples within the imaging plane.

48. A system as recited in any of the preceding embodiments: wherein each sub-region comprises a square region having four corners; wherein dividing the image into sub-regions comprises: calculating the sum of the distances from each corner to the first transmitting element and a second receiving element in the array; assigning windowed time samples having start and end times corresponding to the calculated distances; and muting time samples outside said start and end times.

49. A system as recited in any of the preceding embodiments, wherein imaging each sub-region comprises: generating an inter-element transfer matrix of the received backscatter signal; generating a generalized time-reversal (TR) matrix from the inter-element transfer matrix of the sub-region; and generating a pseudo-spectrum for each sub-region.

50. A system as recited in any of the preceding embodiments, wherein generating an inter-element transfer matrix comprises calculating the inter-element transfer matrix as a function of one or more of the following: the electro-mechanical response of each transducer element in the array, the diffraction impulse response of each transducer element in the array, the attenuation in the target region, or the finite size effects of the array of transducer elements.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. A method of performing ultrasound imaging of a medium, comprising:
    exciting a first transducer element in an array of transducer elements to direct an ultrasound signal into a target region within the medium;
    receiving a backscatter signal from the target region within the medium with the array of transducer elements;
    generating an inter-element transfer matrix of the received backscatter signal;
    generating a generalized time-reversal (TR) matrix from the inter-element transfer matrix; and
    generating a pseudo-spectrum for generalized TR-Music imaging of the target region,
    wherein generating the inter-element transfer matrix comprises calculating the inter-element transfer matrix as a function of an electro-mechanical response of each transducer element in the array, a diffraction response of each transducer element in the array, and attenuation in the target region.

2. A method as recited in claim 1, wherein the diffraction response of each transducer element is a function of finite size effects of the array of transducer elements.

3. A method as recited in claim 2,
    wherein the inter-element transfer matrix is calculated as according to a function $a_i(r_0,\omega)$ over a surface of a transducer element i,
    wherein:

$$a_i(r_0, \omega) = \int\int_{S_i} g_0(r \mid r_0)ds,$$

and
    wherein $\omega$ is an angular frequency, ds is a delimiter of integration, $g_0(\omega,r|r_0)$ is the free-space Green's function, $a_i(r_0,\omega)$ is the integral of the Green's function over the surface of element i, and r corresponds to a location of a wavefield resulting from a point source at a location $r_0$.

4. A method as recited in claim 1,
wherein the inter-element transfer matrix K is calculated according to the function:

$$K = \frac{2ik^4}{\omega\kappa_0} F(\omega) \int\int\int_{V_0} \gamma_\kappa(r_0) A_{r_0} A_{r_0}^T dv_0;$$

and
wherein i is an imaginary unit, k is a complex wave number, $\omega$ is an angular frequency, $\kappa_0$ is an average compressibility of the medium, $F(\omega)$ is an electromechanical transfer function, $V_0$ is a scattering volume, $\gamma_\kappa$ is a fluctuation equation, $r_0$ is a location, $dv_0$ is a delimiter of integration, and the superscript T in $A_{r_a}^T$ denotes that $A_{r_0}^T$ is the transpose of $A_{r_0}$ which is an N-dimensional column vector given by:

$$[a_1(r_0,\omega) a_2(r_0,\omega) \ldots a_N(r_0,\omega)].$$

5. A method as recited in claim 1,
wherein the generalized time-reversal matrix is calculated according to:

$$T = \frac{-4k^8}{(\omega\kappa_0)^2} |F(\omega)|^2 \sum_{m=1}^{M} \sum_{m'=1}^{M} \Lambda_{m,m'} A_{r_m}^* A_{r'_m}^T,$$

wherein $$A_{r_m}^T = [a_1(r_m, \omega) \quad a_2(r_m, \omega) \quad \ldots, \quad a_N(r_m, \omega)];$$

and $$\Lambda_{m,m'} = \gamma_\kappa(r_m)\gamma_\kappa(r'_m)\langle A_{r_m}, A_{r'_m}\rangle,$$

and
wherein i is an imaginary unit, k is a complex wave number, $\omega$ is an angular frequency, $\kappa_0$ is an average compressibility of the medium, $F(\omega)$ is an electromechanical transfer function, m and m' are variables which range from 1 to M, M the number of scatterers, $A^*_{r_m}$ corresponds to vectors associated with the scatterers, and $A_{r'_m}^T$ is the transpose of $A_{r'_m}$.

6. A method as recited in claim 5,
wherein the pseudo-spectrum PS(r) is calculated according to the equation:

$$PS(r) = \frac{1}{\sum_{m_0=M+1}^{N} |\langle \mu^*_{m_0}, \Lambda_r\rangle|^2},$$

and
wherein M corresponds to a number of scatterers in the target region, N corresponds to the number transducer elements in the array, $\mu^*_{m_0}$ is the complex-conjugate of $\mu_{m_0}$ which corresponds to an eigenvector with a zero eigenvalue, and $A_r$ corresponds to vectors associated with r which corresponds to a location of a wavefield resulting from a point source at a location $r_0$.

7. A method as recited in claim 1,
wherein the inter-element transfer matrix is calculated as according to a function $g_0(\omega, r|r_0)$,
wherein:

$$g_0(\omega, r|r_0) = \frac{\exp - i\underline{k}|r-r_0|}{4\pi|r-r_0|}; \quad \text{and}$$

$$\underline{k} = \frac{\omega}{c} - i\alpha,$$

and
wherein k is a complex wave number, r corresponds to a location of a wavefield resulting from a point source at a location $r_0$, exp( ) is Euler's number raised to the power of the quantity in the parenthesis, $k=\omega/c$ is a real wave number, $\omega$ is angular frequency, $\alpha$ is the amplitude attenuation coefficient, c is the average sound speed, and i is the imaginary unit.

8. An ultrasound imaging system, comprising:
(a) a processor; and
(b) programming executable on said processor for:
   (i) exciting a first transducer element in an array of transducer elements to direct an ultrasound signal into a target region of tissue;
   (ii) receiving a backscatter signal from the target region with the array of transducer elements; and
   (iii) performing time reversal imaging by:
      generating an inter-element transfer matrix of the received backscatter signal;
      generating a generalized time-reversal (TR) matrix from the inter-element transfer matrix; and
      generating a pseudo-spectrum for generalized TR-Music imaging of the target region,
   wherein generating the inter-element transfer matrix comprises calculating the inter-element transfer matrix as a function of an electro-mechanical response of each transducer element in the array, a diffraction response of each transducer element in the array, and attenuation in the target region.

9. A system as recited in claim 8, wherein finite size effects of the array of transducer elements are factored in calculating the inter-element response matrix.

10. A system as recited in claim 8,
wherein the inter-element transfer matrix K is calculated according to the equation:

$$K = \frac{2ik^4}{\omega\kappa_0} F(\omega) \int\int\int_{V_0} \gamma_\kappa(r_0) A_{r_0} A_{r_0}^T dv_0,$$

and
wherein i is an imaginary unit, k is a complex wave number, $\omega$ is an angular frequency, $\kappa_0$ is an average compressibility of the medium, $F(\omega)$ is an electromechanical transfer function, $V_0$ is a scattering volume, $\gamma_\kappa$ is a fluctuation equation, $r_0$ is a location, $dv_0$ is a delimiter of integration, and the superscript T in $A_{r_0}^T$ denotes that $A_{r_0}^T$ is the transpose of $A_{r_0}$ which is an N-dimensional column vector given by:

$$[a_1(r_0,\omega) a_2(r_0,\omega) \ldots a_N(r_0,\omega)].$$

11. A system as recited in claim 8,
wherein the generalized time-reversal matrix is calculated according to:

$$T = \frac{-4k^8}{(\omega \kappa_0)^2}|F(\omega)|^2 \sum_{m=1}^{M}\sum_{m'=1}^{M} \Lambda_{m,m'} A^*_{r_m} A^T_{r'_m},$$

wherein $$A^T_{r_m} = [\, a_1(r_m, \omega) \quad a_2(r_m, \omega) \quad \ldots \quad a_N(r_m, \omega)\,];$$

and $$\Lambda_{m,m'} = \gamma_\kappa(r_m)\gamma_\kappa(r'_m)\langle A_{r_m}, A_{r'_m}\rangle,$$

and
wherein i is an imaginary unit, k is a complex wave number, ω is an angular frequency, $\kappa_0$ is an average compressibility of the medium, F(ω) is an electromechanical transfer function, m and m' are variables which range from 1 to M, M the number of scatterers, $A^*_{r_m}$ corresponds to vectors associated with the scatterers, and $A_{r'_m}^T$ is the transpose of $A_{r'_m}$.

12. A system as recited in claim 8,
wherein the inter-element transfer matrix is calculated as according to a function $g_0(\omega, r|r_0)$,
wherein:

$$g_0(\omega, r\mid r_0) = \frac{\exp -ik|r - r_0|}{4\pi|r - r_0|};$$

$$\underline{k} = \frac{\omega}{c} - i\alpha,$$

and
wherein k is a complex wave number, r and $r_0$ are locations, exp( ) is Euler's number raised to the power of the quantity in the parenthesis, k=ω/c is the real wave number, ω is the angular frequency, α is the amplitude attenuation coefficient, c is the average sound speed, and i is the imaginary unit.

13. A system as recited in claim 8,
wherein the inter-element transfer matrix is calculated as according to the function $a_i(r_0,\omega)$ over a surface of a transducer element i,
wherein:

$$a_i(r_0, \omega) = \iint_{S_i} g_0(r\mid r_0)ds,$$

and
wherein w is an angular frequency, ds is a delimiter of integration, is $g_0(\omega,r|r_0)$ is the free-space Green's function, $a_i(r_0,\omega)$ is the integral of the Green's function over the surface of element i, and r corresponds to a location of a wavefield resulting from a point source at a location $r_0$.

\* \* \* \* \*

UNITED STATES PATENT AND TRADEMARK OFFICE
CERTIFICATE OF CORRECTION

PATENT NO. : 9,955,943 B2  
APPLICATION NO. : 14/339780  
DATED : May 1, 2018  
INVENTOR(S) : Lianjie Huang et al.

Page 1 of 1

It is certified that error appears in the above-identified patent and that said Letters Patent is hereby corrected as shown below:

In the Claims

Column 31, Line 11, Claim 4     delete "$dv_0$;"
insert -- $dv_0$, --

Column 31, Line 21, Claim 4     delete " $A_{r_a}^T$ "
insert -- $A_{r_0}^T$ --

Column 32, Lines 7-8, Claim 7   delete " $g_0(\omega, r \mid r_0) = \dfrac{\exp - ik|r - r_0|}{4\pi|r - r_0|}$ "
insert -- $g_0(\omega, \mathbf{r} \mid \mathbf{r_0}) = \dfrac{\exp(-i\underline{k}|\mathbf{r} - \mathbf{r_0}|)}{4\pi|\mathbf{r} - \mathbf{r_0}|}$ --

Column 32, Lines 7-8, Claim 12  delete " $g_0(\omega, r \mid r_0) = \dfrac{\exp - ik|r - r_0|}{4\pi|r - r_0|}$ "
insert -- $g_0(\omega, \mathbf{r} \mid \mathbf{r_0}) = \dfrac{\exp(-i\underline{k}|\mathbf{r} - \mathbf{r_0}|)}{4\pi|\mathbf{r} - \mathbf{r_0}|}$ --

Signed and Sealed this  
Twenty-seventh Day of August, 2019

Andrei Iancu  
*Director of the United States Patent and Trademark Office*